US008288428B2

(12) United States Patent
Wang et al.

(10) Patent No.: US 8,288,428 B2
(45) Date of Patent: Oct. 16, 2012

(54) COMPOUNDS AS CANNABINOID RECEPTOR LIGANDS

(75) Inventors: Xueqing Wang, Evanston, IL (US); Jennifer M. Frost, Gurnee, IL (US); Michael J. Dart, Highland Park, IL (US); Bo Liu, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 286 days.

(21) Appl. No.: 12/732,428

(22) Filed: Mar. 26, 2010

(65) Prior Publication Data

US 2010/0249087 A1 Sep. 30, 2010

Related U.S. Application Data

(60) Provisional application No. 61/163,986, filed on Mar. 27, 2009.

(51) Int. Cl.
A61K 31/4155 (2006.01)
A61K 31/415 (2006.01)
C07D 231/40 (2006.01)
C07D 403/12 (2006.01)
(52) U.S. Cl. .................. 514/404; 514/210.2; 548/372.5
(58) Field of Classification Search .................. 514/404, 514/210.2; 548/372.5
See application file for complete search history.

(56) References Cited

U.S. PATENT DOCUMENTS

| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2008/0312435 | A1* | 12/2008 | Saito et al. ..................... 544/133 |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| EP | 1820504 A1 | 8/2007 |
| WO | WO9507271 A1 | 3/1995 |
| WO | WO9710223 A1 | 3/1997 |
| WO | WO2005099353 A2 | 10/2005 |
| WO | WO2006008754 A1 | 1/2006 |
| WO | WO2006051704 | 5/2006 |
| WO | WO 2006051704 A1 * | 5/2006 |
| WO | WO2008063781 | 5/2008 |

OTHER PUBLICATIONS

CAS Registry No. 1061668-81-2, which entered STN on Oct. 15, 2008.*
Arevalo-Martin, A., et al., "Therapeutic Action of Cannabinoids in a Murine Model of Multiple Sclerosis," Journal of Neuroscience, 2003, vol. 23 (7), pp. 2511-2516.
Benito C., et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Bouchard J.F., et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle W.J., et al., "Osteoclast Differentiation and Activation," Nature, 2003, vol. 423 (6937), pp. 337-342.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Buckley N.E., et al., "Immunomodulation by Cannabinoids is Absent in Mice Deficient for the Cannabinoid CB2 Receptor," European Journal of Pharmacology, 2000, vol. 396, pp. 141-149.
Carlisle S.J., et al., "Differential Expression of the CB2 Cannabinoid Receptor by Rodent Macrophages and Macrophage-like Cells in Relation to Cell Activation," International Immunopharmacology, 2002, vol. 2, pp. 69.
Carrier E.J., et al., "Endocannabinoids in Neuroimmunology and Stress," Current Drug Targets—CNS and Neurological Disorders, 2005, vol. 4, pp. 657-665.

(Continued)

*Primary Examiner* — Joseph Kosack
*Assistant Examiner* — Matthew Coughlin
(74) *Attorney, Agent, or Firm* — Nancy J. Gettel; Andrew M. Parial

(57) ABSTRACT

Disclosed herein are cannabinoid receptor ligands of formula (I)

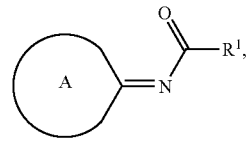

wherein Ring A and $R^1$ are as defined in the specification. Compositions comprising such compounds, and methods for treating conditions and disorders using such compounds and compositions are also described.

13 Claims, No Drawings

OTHER PUBLICATIONS

Casanova M.L., et al., "Inhibition of Skin Tumor Growth and Angiogenesis in vivo by Activation of Cannabinoid Receptors," Journal of Clinical Investigation, 2003, vol. 111 (1), pp. 43-50.

Cichewicz D.L., "Synergistic Interactions Between Cannabinoid and Opioid Analgesics," Life Sciences, 2004, vol. 74 (11), pp. 1317-1324.

Clayton N., et al., "CB1 and CB2 Cannabinoid Receptors are Implicated in Inflammatory Pain," Pain, 2002, vol. 96 (3), pp. 253-260.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Filippo C.D., et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Foster, A. B. et al., "Deuterium Isotope Effects in the Metabolism of Drugs and Xenobiotics: Implications for Drug Design," Advances in Drug Research, 1985, vol. 14, pp. 2-36.

Galiégue S., et al., "Expression of Central and Peripheral Cannabinoid Receptors in Human Immune Tissues and Leukocyte Subpopulations," European Journal of Biochemistry, 1995, vol. 232 (1), pp. 54-61.

Greene T.W., et al., "Protection for the Amino group," Protective Groups in Organic Synthesis, 1999, Third Edition, pp. 494-653.

Grotenhermen F., et al., "IACM 2nd Conference on Cannabinoids in Medicine," Expert Opinion in Pharmacotherapy, 1976, vol. 4 (12), pp. 2367-2371.

Hanus L., et al., "HU-308: A Specific Agonist for CB 2, a Peripheral Cannabinoid Receptor," Proceedings of the National Academy of Science, 1999, vol. 96, pp. 14228-14233.

Hohmann A.G., et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.

Ibrahim M.M., et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim M.M., et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

Ihenetu K., et al., "Inhibition of Interleukin-8 Release in the Human Colonic Epithelial Cell Line HT-29 by Cannabinoids," European Journal of Pharmacology, 2003, vol. 458 (1-2), pp. 207-215.

ISR for Application No. PCT/US2010/028794, mailed Jul. 20, 2010, 3 pages.

Julien B., et al., "Antifibrogenic Role of the Cannabinoid Receptor CB2 in the Liver," Gastroenterology, 2005, vol. 128, pp. 742-755.

Karsak M., et al., "Cannabinoid Receptor Type 2 Gene is Associated with Human Osteoporosis," Human Molecular Genetics, 2005, vol. 14 (22), pp. 3389-3396.

Kato, S. et al., "Synthesis of Deuterated Mosapride Citrate," Journal of Labelled Compounds and Radiopharmaceuticals, 1995, vol. 36 (10), pp. 927-932.

Kushner et al., "Pharmacological uses and perspectives of heavy water and deuterated compounds," Canadian Journal of Physiology and Pharmacology, 1999, vol. 77 (2), pp. 79-88.

Lepicier P., et al., "Endocannabinoids Protect the RAt Isolated Heart Against Ischaemia," British Journal of Pharmacology, 2003, vol. 139, pp. 805-815.

Lizondo, J. et al., "Linezolid: Oxazolidinone antibacterial," Drugs of the Future, 1996, vol. 21 (11), pp. 1116-1123.

Lotersztajn S., et al., "Hepatic Fibrosis: Molecular Mechanisms and Drug Targets," Annual Review of Pharmacology and Toxicology, 2005, vol. 45, pp. 605-628.

Malan T.P., et al., "CB2 Cannabinoid Receptor-Mediated Peripheral Antinociception," Pain, 2001, vol. 93, pp. 239-245.

Mallesham, B. et al., "Highly Efficient Cui-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Maresz K., et al., "Modulation of the Cannabinoid CB2 Receptor in Microglial Cells in Response to Inflammatory Stimuli," Journal of Neurochemistry, 2005, vol. 95, pp. 437-445.

Mathison R., et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip R.J., et al., "Targeting CB2 Cannabinoid Receptors as a Novel Therapy to Treat Malignant Lymphoblastic Disease," Blood, 2002, vol. 15 (2), pp. 627-634.

Miyaura N., ed., Topics in Current Chemistry: Cross Coupling Reactions, Springer, 2002, Table of Contents.

Nackley A.G., et al., "Selective Activation of Cannabinoid CB2 Receptors Suppresses Spinal for Protein Expression and Pain Behavior in a Rat Model of Inflammation," Neuroscience, 2003, vol. 119, pp. 747-757.

Negishi E., et al., eds., Handbook of Organopalladium Chemistry for Organic Synthesis, vol. 1, John Wiley & Sons, 2002, Table of Contents.

Ni X., et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Patel H.J., et al., "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.

Pertwee R.G., "Cannabinoids and Multiple Sclerosis," Pharmacology & Therapeutics, 2002, vol. 95, pp. 165-174.

Poste G. et al., "Lipid Vesicles as Carriers for Introducing Biologically Active Materials into Cells," Methods in Cell Biology, 1976, vol. 14, pp. 33-71.

Quartilho A., et al., "Inhibition of Inflammatory Hyperalgesia by Activation of Peripheral CB2 Cannabinoid Receptors," Anesthesiology, 2003, vol. 99, pp. 955-960.

Ralston S.H., "Regulation of Bone Mass, Bone Loss and Osteoclast Activity by Cannabinoid Receptors," Nature Medicine, 2005, vol. 11 (7), pp. 774-779.

Ramirez B.G., et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Sanchez C., et al., "Inhibition of Glioma Growth in Vivo by Selective Activation of the CB2 Cannabinoid Receptor1," Cancer Research, 2001, vol. 61, pp. 5784-5789.

Steffens S., et al., "Low Dose Oral Cannabinoid Therapy Reduces Progression of Atherosclerosis in Mice," Nature, 2005, vol. 434, pp. 782-786.

Thomson, J.F., "Physiological Effects of D20 in Mammals," Annals of the New York Academy of Sciences, 1960, vol. 84, pp. 736-744.

Valenzano K.J., et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.

Warhurst A.C., et al., "Interferon Gamma Induces Differential Upregulation of Alpha and Beta Chemokine Secretion in Colonic Epithelial Cell Lines," Gut, 1998, vol. 42 (2), pp. 208-213.

Wright K., et al., "Differential Expression of Cannabinoid Receptors in the Human Colon: Cannabinoids Promote Epithelial Wound Healing," Gastroenterology, 2005, vol. 129 (2), pp. 437-453.

Yoshihara S., et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara S., et al., "Endogenous Cannabinoid Receptor Agonists Inhibit Neurogenic Inflammations in Guinea Pig Airways," Allergy and Immunology, 2005, vol. 138, pp. 80-87.

Yoshihara S., et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

\* cited by examiner

US 8,288,428 B2

COMPOUNDS AS CANNABINOID RECEPTOR LIGANDS

This application claims priority to U.S. application Ser. No. 61/163,986 filed Mar. 27, 2009, and is incorporated herein by reference in its entirety.

TECHNICAL FIELD AND BACKGROUND

Compounds that are cannabinoid receptor ligands, compositions comprising such compounds, and methods of treating conditions and disorders using such compounds and compositions are disclosed.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY OF THE INVENTION

Provided herein are compounds of formula (I)

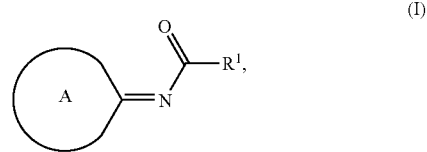

(I)

or pharmaceutically acceptable salts, solvates, prodrugs, salts of prodrugs, or any combinations thereof, wherein $R^1$ is aryl, heteroaryl, heterocycle, cycloalkyl, or cycloalkenyl; wherein each ring is independently substituted by one $R^x$ group and optionally further substituted with 1, 2, 3, or 4 $R^y$ group(s);

$R^x$ is —C(=NOR$^f$)R$^a$, —(CR$^{1a}$R$^{1b}$)$_{q1}$-A$^1$, alkenyl, or alkynyl; wherein the alkenyl and the alkynyl are substituted with one or two A$^2$ groups;

each $R^y$ is independently G$^{1d}$, alkyl, alkenyl, alkynyl, halogen, haloalkyl, =N—CN, =N—OR$^f$, NO$_2$, —CN, oxo, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

A$^1$ is —OR$^a$, —OC(O)R$^a$, —OC(O)N(R$^b$)(R$^c$), —N(R$^b$)(R$^k$), —C(O)O(R$^a$), —C(O)R$^a$, —S(O)$_2$R$^d$, —S(O)R$^d$, —SR$^d$, —C(O)N(R$^b$)(R$^c$), —C(S)N(R$^b$)(R$^c$), —S(O)$_2$N(R$^b$)(R$^c$), —C(=NOR$^f$)R$^a$, —CN, —N(R$^c$)C(O)R$^a$, —N(R$^c$)C(O)OR$^d$, —N(R$^c$)S(O)$_2$R$^d$, —N(R$^c$)C(O)N(R$^b$)(R$^c$), —N(R$^c$)S(O)$_2$N(R$^b$)(R$^c$), G$^{1a}$ or G$^{1b}$;

each occurrence of A$^2$ is independently —OR$^a$, —OC(O)R$^a$, —OC(O)N(R$^b$)(R$^c$), —N(R$^b$)(R$^k$), —C(O)O(R$^a$), —C(O)R$^a$, —S(O)$_2$R$^d$, —S(O)R$^d$, —SR$^d$, —C(O)N(R$^b$)(R$^c$), —C(S)N(R$^b$)(R$^c$), —S(O)$_2$N(R$^b$)(R$^c$), —C(=NOR$^f$)R$^a$, —CN, —N(R$^c$)C(O)R$^a$, —N(R$^c$)C(O)OR$^d$, —N(R$^c$)S(O)$_2$R$^d$, —N(R$^c$)C(O)N(R$^b$)(R$^c$), —N(R$^c$)S(O)$_2$N(R$^b$)(R$^c$), or G$^{1c}$;

G$^{1a}$ is a 4-, 5-, 6-, or 7-membered monocyclic heterocycle having zero double bond and one or two heteroatoms in the ring, wherein each ring is substituted with 1, 2, or 3 substituents independently selected from the group consisting of oxo, alkyl, alkenyl, alkynyl, haloalkyl, —OH, alkoxy, —C(O)O(alkyl), and hydroxyalkyl;

G$^{1b}$ is optionally substituted cycloalkyl or optionally substituted cycloalkenyl;

G$^{1c}$ is cycloalkyl, cycloalkenyl, aryl, heterocycle, or heteroaryl;

each ring as represented by G$^{1b}$ and G$^{1c}$ is optionally substituted with 1, 2, 3, 4, 5, or 6 substituents independently selected from the group consisting of oxo, alkyl, alkenyl, alkynyl, halogen, haloalkyl, =N—CN, —C(=NOR$^f$)R$^a$, =N—OR$^f$, —CN, NO$_2$, oxo, —OR$^a$, —OC(O)R$^a$, —OC(O)N(R$^b$)(R$^c$), —S(O)R$^d$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^c$)C(O)R$^a$, —N(R$^c$)S(O)$_2$R$^d$, —N(R$^c$)C(O)O(R$^a$), —N(R$^c$)S(O)$_2$N(R$^b$)(R$^c$), —N(R$^c$)C(O)N(R$^b$)(R$^c$), —(CR$^{1c}$R$^{1d}$)$_{q3}$—OR$^a$, —(CR$^{1c}$R$^{1d}$)$_{q3}$—OC(O)R$^a$, —(CR$^{1c}$R$^{1d}$)$_{q3}$—OC(O)N(R$^b$)(R$^c$), —(CR$^{1c}$R$^{1d}$)$_{q3}$—S(O)R$^d$, —(CR$^{1c}$R$^{1d}$)$_{q3}$—S(O)$_2$R$^d$, —(CR$^{1c}$R$^{1d}$)$_{q3}$—S(O)$_2$N(R$^b$)(R$^c$), —(CR$^{1c}$R$^{1d}$)$_{q3}$—C(O)R$^a$, —(CR$^{1c}$R$^{1d}$)$_{q3}$—C(O)OR$^a$, —(CR$^{1c}$R$^{1d}$)$_{q3}$—C(O)N(R$^b$)(R$^c$), —(CR$^{1c}$R$^{1d}$)$_{q3}$—N(R$^b$)(R$^c$), —(CR$^{1c}$R$^{1d}$)$_{q3}$—N(R$^c$)C(O)R$^a$, —(CR$^{1c}$R$^{1d}$)$_{q3}$—N(R$^c$)S(O)$_2$R$^d$, —(CR$^{1c}$R$^{1d}$)$_{q3}$—N(R$^c$)C(O)O(R$^a$), —(CR$^{1c}$R$^{1d}$)$_{q3}$—N(R$^c$)S(O)$_2$N(R$^b$)(R$^c$), —(CR$^{1c}$R$^{1d}$)$_{q3}$—N(R$^c$)C(O)N(R$^b$)(R$^c$), and —(CR$^{1c}$R$^{1d}$)$_{q3}$—CN;

R$^a$ and R$^c$, at each occurrence, are each independently hydrogen, alkyl, haloalkyl, —(CR$^{1a}$R$^{1b}$)$_{q3}$-A$^3$, or —(CR$^{1a}$R$^{1b}$)$_{q3}$-G$^{1d}$;

R$^b$, at each occurrence, is independently hydrogen, alkyl, haloalkyl, alkoxyalkyl, monocyclic cycloalkyl, —(CR$^{1c}$R$^{1d}$)$_{q3}$-(monocyclic cycloalkyl), or haloalkoxyalkyl;

R$^d$, at each occurrence, is independently alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

G$^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —N(R$^h$)$_2$, —CN, oxo, alkyl, haloalkyl, alkoxy, haloalkoxy, halogen, and —OH;

each occurrence of A$^3$ is independently C(O)R$^h$, —S(O)$_2$R$^e$, —C(O)N(R$^h$)$_2$, —C(S)N(R$^h$)$_2$, —S(O)$_2$N(R$^h$)$_2$, —C(=NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^h$, or —N(R$^h$)$_2$;

R$^e$, at each occurrence, is independently C$_1$-C$_4$ alkyl, C$_1$-C$_4$ haloalkyl, monocyclic cycloalkyl, monocyclic heterocycle, or —(CR$^{1c}$R$^{1d}$)$_{q3}$-(monocyclic cycloalkyl);

R$^f$, at each occurrence, is independently hydrogen, C$_1$-C$_4$ alkyl, C$_1$-C$_4$ haloalkyl, monocyclic heterocycle, monocyclic cycloalkyl, or —(CR$^{1c}$R$^{1d}$)$_{q3}$-(monocyclic cycloalkyl);

R$^k$ is haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^{k'}$ is hydrogen, alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^h$, at each occurrence, is independently hydrogen, C$_1$-C$_4$ alkyl, C$_1$-C$_4$ haloalkyl, monocyclic heterocycle, monocyclic cycloalkyl, or —(CR$^{1c}$R$^{1d}$)$_{q3}$-(monocyclic cycloalkyl);

Ring A represents formula (a), (b), (c), or (d)

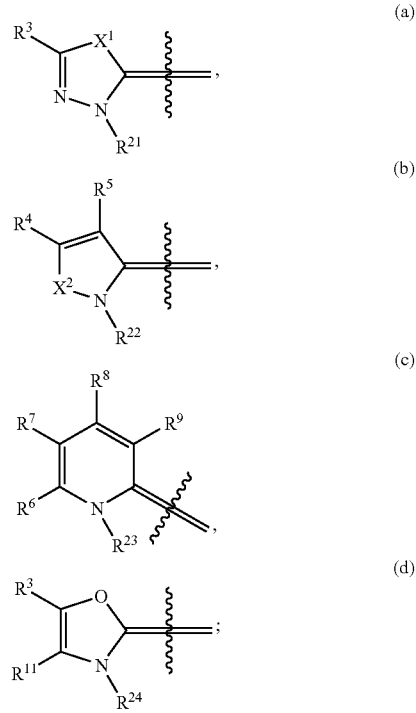

R$^{21}$, R$^{22}$, R$^{23}$, and R$^{24}$ are each independently alkyl, alkenyl, alkynyl, haloalkyl, —(CR$^{2a}$R$^{2b}$)$_{q4}$—OH, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$—C(O)—R$^a$, —(CR$^{2a}$R$^{2b}$)$_{q5}$—C(O)O(R$^a$), —(CR$^{2a}$R$^{2b}$)$_{q5}$—C(=N—OR$^f$)R$^a$, —(CR$^{2a}$R$^{2b}$)$_{q5}$—SO$_2$—R$^d$, —(CR$^{2a}$R$^{2b}$)$_{q5}$-G$^{2b}$, —(CR$^{2a}$R$^{2b}$)$_{q5}$—C(O)N(R$^b$)(R$^c$), or —(CR$^{2a}$R$^{2b}$)$_{q5}$—CN;

each occurrence of G$^{2a}$ is independently cycloalkyl, heterocycle, aryl, or heteroaryl;

G$^{2b}$ is a monocyclic cycloalkyl, monocyclic cycloalkenyl, thienyl, or phenyl; each of which is optionally fused with a benzo, a monocyclic cycloalkyl, a monocyclic cycloalkenyl, a monocyclic heterocycle, or a monocyclic heteroaryl;

G$^{2a}$ and G$^{2b}$, at each occurrence, are each independently unsubstituted or substituted with 1, 2, 3, 4, 5, or 6 substituents independently selected from the group consisting of oxo, alkyl, halogen, —OH, alkoxy, haloalkoxy, and haloalkyl;

R$^3$, R$^4$, R$^5$, R$^6$, R$^7$, R$^8$, R$^9$, R$^{11}$, and R$^{12}$ are each independently G$^3$, hydrogen, alkyl, alkenyl, alkynyl, —NO$_2$, —CN, halogen, —OR$^h$, —N(R$^h$)$_2$, —C(O)R$^h$, —C(O)O(R$^h$), haloalkyl, —(CR$^{3a}$R$^{3b}$)$_{q6}$—OR$^h$, —(CR$^{3a}$R$^{3b}$)$_{q6}$—N(R$^h$)$_2$, —(CR$^{3a}$R$^{3b}$)$_{q6}$—C(O)R$^h$, or —(CR$^{3a}$R$^{3b}$)$_{q6}$—C(O)O(R$^h$);

G$^3$, at each occurrence, is independently cycloalkyl, cycloalkenyl, aryl, heterocycle or heteroaryl, wherein each G$^3$ is independently unsubstituted or substituted with 1, 2, 3 or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, =N—CN, =N—OR$^h$, oxo, —OR$^h$, —OC(O)R$^h$, —OC(O)N(R$^h$)$_2$, —S(O)$_2$R$^e$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^h$, —N(R$^h$)S(O)$_2$R$^e$, —N(R$^h$)C(O)O(R$^e$), and —N(R$^h$)C(O)N(R$^h$)$_2$;

R$^{1a}$, at each occurrence, is independently hydrogen, halogen, C$_1$-C$_4$ alkyl, or C$_1$-C$_4$ haloalkyl;

$R^{1b}$, at each occurrence, is independently hydrogen, halogen, $C_1$-$C_4$ alkyl, $C_1$-$C_4$ haloalkyl, —$OR^h$, —$N(R^h)_2$, —$N(R^h)C(O)R^h$, —$N(R^h)C(O)OR^e$, or —$N(R^h)S(O)_2R^e$;

$R^{1c}$, $R^{1d}$, $R^{2a}$, $R^{2b}$, $R^{2c}$, $R^{2d}$, $R^{3a}$ and $R^{3b}$, at each occurrence, are each independently hydrogen, halogen, $C_1$-$C_4$ alkyl, or $C_1$-$C_4$ haloalkyl;

$X^1$ and $X^2$ are independently O, S, or $N(R^{10})$ wherein $R^{10}$ is alkyl, alkoxyalkyl, haloalkoxyalkyl, or haloalkyl;

q1 and q3, at each occurrence, are each independently 1, 2, 3, or 4;

q4, at each occurrence, is independently 2, 3, 4, or 5;

q5 and q6, at each occurrence, are each independently 1, 2, 3, 4, 5, or 6; and the monocyclic cycloalkyl and the monocyclic heterocycle, as a substituent or as part of a substituent, of $R^b$, $R^e$, $R^f$, and $R^h$, are each independently unsubstituted or substituted with 1, 2, 3, or 4 substituents independently selected from the group consisting of oxo, $C_1$-$C_4$ alkyl, halogen, —OH, $C_1$-$C_4$ alkoxy, $C_1$-$C_4$ haloalkoxy, and $C_1$-$C_4$ haloalkyl;

with the proviso that when $R^x$ is —$(CR^{1a}R^{1b})_{q1}$-$A^1$, $R^{1a}$ and $R^{1b}$ are each independently hydrogen or alkyl, and $A^1$ is $OR^a$ wherein $R^a$ is $G^{1d}$, then $G^{1d}$ is other than phenyl; and with the further proviso that when $R^x$ is —$(CR^{1a}R^{1b})_{q1}$-$A^1$, $R^{1a}$ and $R^{1b}$ are each independently hydrogen or alkyl, and $A^1$ is $OC(O)R^a$, then $R^a$ is other than alkyl.

Another aspect relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s). Such compositions can be administered in accordance with a method of the invention, typically as part of a therapeutic regimen for treatment or prevention of conditions and disorders related to cannabinoid (CB) receptor subtype $CB_2$. More particularly, the method is useful for treating conditions related to neuropathic pain, nociceptive pain, post-operative pain, osteoarthritis pain, cancer pain, inflammatory pain, cancer pain, lower back pain, eye pain, inflammatory disorders, immune disorders, neurological disorders, cancers of the immune system, respiratory disorders, obesity, diabetes, cardiovascular disorders, or for providing neuroprotection.

Further provided herein are the use of present compounds or pharmaceutically acceptable salts, solvates, or salts of solvates thereof, in the manufacture of a medicament for the treatment of the disease conditions described above, alone or in combination with one or more pharmaceutically acceptable carrier(s), particularly for the treatment of pain such as, but not limited to, neuropathic pain, nociceptive pain, osteoarthritis pain, inflammatory pain, cancer pain, lower back pain, eye pain, and post-operative pain, or combinations thereof.

The compounds, compositions comprising the compounds, and methods for treating or preventing conditions and disorders by administering the compounds are further described herein. These and other objectives of the invention are described in the following paragraphs. These objectives should not be deemed to narrow the scope of the invention.

DETAILED DESCRIPTION OF THE INVENTION

Provided are compounds of formula (I)

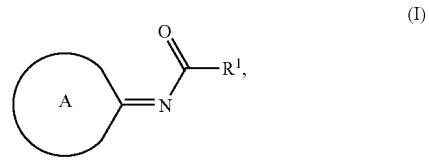

wherein A and $R^1$ are as defined above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formulae herein. Definition of a variable on each occurrence is independent of its definition at another occurrence. Further, combinations of variables are permissible only if such combinations result in stable compounds. Stable compounds are compounds that can be isolated from a reaction mixture.

A. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" as used herein, means a straight or branched hydrocarbon chain containing from 2 to 4 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 3-methylbut-1-enyl, 4-pentenyl, 5-hexenyl, 2-heptenyl, 2-methyl-1-heptenyl, and 3-decenyl.

The term "alkenylene" denotes a divalent group derived from a straight or branched hydrocarbon chain of 2, 3, or 4 carbon atoms and contains at least one carbon-carbon double. Representative examples of alkenylene include, but are not limited to, —CH=CH— and —$CH_2$CH=CH—.

The term "alkoxy" as used herein, means an alkyl group, as defined herein, appended to the parent molecular moiety through an oxygen atom. The term "$C_1$-$C_4$ alkoxy" as used herein, means a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-methoxyethyl, 3-methoxy-3-methylbutyl, 2-methoxypropyl, 3-methoxypropyl, 2-ethoxyethyl, 2-methoxyethyl, 3-ethoxypropyl, and methoxymethyl.

The term "alkyl" as used herein, means a saturated, straight or branched hydrocarbon chain containing from 1 to 10 carbon atoms. The terms "$C_1$-$C_4$ alkyl" and "$C_1$-$C_6$ alkyl" as used herein, means a saturated, straight or branched hydrocarbon chain containing from 1 to 4 and from 1 to 6 carbon atoms respectively. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" means a divalent group derived from a saturated, straight or branched hydrocarbon chain of from 1 to 10 carbon atoms. Representative examples of alkylene include, but are not limited to, —$CH_2$—, —$CH(CH_3)$—, —$CH(C_2H_5)$, —$CH(CH(CH_3)(C_2H_5))$—, —$C(H)(CH_3)$ $CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched hydrocarbon chain containing from 2 to 10 carbon atoms and containing at least one carbon-carbon triple bond. The term "$C_2$-$C_4$ alkynyl" as used herein, means a straight or branched hydrocarbon chain containing from 2 to 4 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic, and tricyclic aryls are attached to the parent molecular moiety through any carbon atom contained within the phenyl, bicyclic, and tricyclic aryls respectively.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a,4,5,6, 7,7a-hexahydro-1H-indenyl, 4,5,6,7-tetrahydro-3aH-indene, and octahydronaphthalenyl. The cycloalkenyl groups are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl. The term "$C_3$-$C_6$ cycloalkyl" as used herein, means a monocyclic cycloalkyl having 3, 4, 5, or 6 carbon atoms in the ring. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups may contain one or two alkylene bridges of 1, 2, 3, or 4 carbon atoms, wherein each bridge links two non-adjacent atoms within the groups. Examples of such bridged cycloalkyls include, but are not limited to, 6,6-dimethylbicyclo[3.1.1]heptyl (including 6,6-dimethylbicyclo[3.1.1]hept-2-yl), bicyclo[2.2.1]heptyl, bicyclo[3.1.1]heptyl, bicyclo[2.2.2]octyl, bicyclo[3.3.1]nonyl, adamantyl(tricyclo[3.3.1.1$^{3,7}$]decane), and noradamantyl(octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups can be appended to the parent molecular moiety through any substitutable carbon atom of the groups.

The term "halo" or "halogen" as used herein, means —Cl, —Br, —I or —F.

The term "haloalkoxy" as used herein, means an alkoxy group, as defined herein, in which one, two, three, four, five, or six hydrogen atoms are replaced by halogen. The term "$C_1$-$C_4$ haloalkoxy" as used herein, means a $C_1$-$C_4$ alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkylene group, as defined herein.

The term "haloalkyl" as used herein, means an alkyl group, as defined herein, in which one, two, three, four, five, six, or seven hydrogen atoms are replaced by halogen. The term "$C_1$-$C_4$ haloalkyl" as used herein, means a $C_1$-$C_4$ alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl (including, but not limited thereto, quinolin-8-yl), and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings may optionally be oxidized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two, or three heteroatoms in the ring selected from the group consisting of O, N, and S. The 6-, 7-, or 8-membered ring contains zero, one, or two double bonds, and one, two, or three heteroatoms in the ring selected from the group consisting of O, N, and S. Representative examples of monocyclic heterocycles include, but are not limited to, azetidinyl (including, but not limited thereto, azetidin-1-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl (including, but not limited thereto, piperidin-1-yl), pyranyl, pyrazolinyl, pyrazolidinyl, pyrrolinyl, pyrrolidinyl (including, but not limited thereto, pyrrolidin-1-yl), tetrahydrofuranyl (including but not limited thereto, tetrahydrofuran-2-yl and tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include, but are not limited to, 1,3-benzodioxol-4-yl, 1,3-benzodithiolyl, 2,3-dihydro-1, 4-benzodioxinyl, 2,3-dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. The heterocycle groups are connected to the parent molecular moiety through any substitutable carbon atom or any substitutable nitrogen atom contained within the group. The monocyclic or bicyclic heterocycle groups may contain an alkenylene bridge of 2, 3, or 4 carbon atoms, or may contain one or two alkylene bridges of 1, 2, 3, or 4 carbon atoms, or combinations thereof, wherein each bridge links two non-adjacent carbon atoms within the groups. Examples of such bridged heterocycles include, but are not limited to, oxaadamantane (2-oxatricyclo[3.3.1.1$^{3,7}$] decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings may optionally be oxidized and the nitrogen atoms may optionally be quarternized.

The term "hydroxyl" or "hydroxy" means an OH group.

The term "hydroxyalkyl" as used herein, means an hydroxy group, as defined herein, appended to the parent molecular moiety through an alkylene group, as defined herein. Non-limiting examples of hydroxyalkyl include 2-hydroxy-2-methylpropyl, 1-hydroxy-1-methylethyl, and 2-hydroxyethyl.

The term "heteroatom" as used herein, means a nitrogen, oxygen, or sulfur atom.

The term "oxo" means =O.

The term "treatment" or "treating" pain as used herein includes acute or chronic pain and means: (1) preventing pain, i.e. causing pain not to develop or occur with less intensity in a subject that may be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

B. COMPOUNDS $CB_2$ ligands have formula (I) as described herein. Particular values of variable groups in compounds of formula (I) are as follows. Such values may be used where appropriate with any of the other values, definitions, claims or embodiments defined hereinbefore or hereinafter.

In compounds of formula (I), $R^1$ has values as disclosed in the Summary of the Invention. In conjunction with any one of the above or below embodiments, certain compounds include those wherein $R^1$ is aryl. Examples of $R^1$ can be aryl, including, but not limited to, phenyl, naphthyl, and tetrahydronaphthalenyl, each of which is substituted as described in the Summary of the Invention.

In conjunction with any one of the above or below embodiments, $R^1$ is phenyl, substituted as described in the Summary, for example, $R^1$ is formula (i)

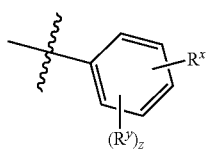

wherein z is 0, 1, 2, 3, or 4, and $R^x$ and $R^y$ are as described generally in the Summary and embodiments hereinafter.

Thus, included herein are compounds of formula (I-i)

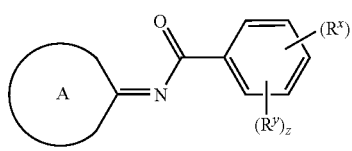

wherein z is 0, 1, 2, 3, or 4, Ring A, $R^x$, and $R^y$ are each described generally in the Summary and in embodiments herein.

In certain embodiments, z is 0, 1, or 2. In certain embodiments, z is 0 or 1.

In certain embodiments, $R^1$ is formula (i) wherein z is 1, for example, such as those represented by formula (ii)

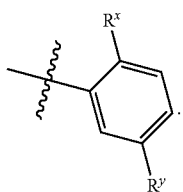

Thus, included herein are certain compounds wherein $R^1$ is formula (ii), as represented by formula (I-ii)

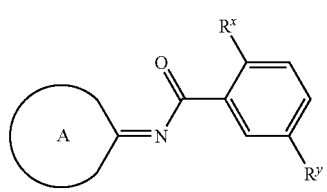

wherein Ring A, $R^x$, and $R^y$ are each described generally in the Summary and in embodiments herein.

In yet other embodiments, $R^1$ is formula (iii)

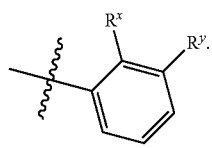

Compounds containing $R^1$ having formula (iii) are represented by formula (I-iii)

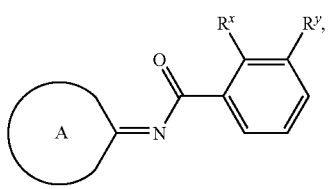

wherein Ring A, $R^x$, and $R^y$ are each described generally in the Summary and in embodiments herein.

In conjunction with any one of the above or below embodiments, $R^1$ is substituted heteroaryl (such as, but not limited thereto, substituted quinolinyl).

In conjunction with any one of the above or below embodiments, $R^1$ is substituted heterocyclic.

In conjunction with any one of the above or below embodiments, $R^1$ is substituted cycloalkyl or substituted cycloalkenyl.

$R^x$ has values as generally described in the Summary. In certain embodiments, $R^x$ is, for example, $-(CR^{1a}R^{1b})_{q1}-A^1$ or alkenyl substituted with one $A^2$ group.

In other embodiments, $R^x$ is, for example, $-(CR^{1a}R^{1b})_{q1}-A^1$.

In yet other embodiments, $R^x$, for example, is alkenyl (such as, but not limited to, 3-methylbut-1-enyl) substituted with one $A^2$ group.

In conjunction with any above or below embodiments, $R^{1a}$, $R^{1b}$, $A^1$, A and q1 are as described in the Summary and herein below. For example, each occurrence of $R^{1a}$ and $R^{1b}$ are each independently hydrogen or $C_1$-$C_4$ alkyl (such as, but not limited to, methyl, ethyl). $A^1$, for example, is $-OR^a$, $-C(O)O(R^a)$, or $G^{1a}$. Certain compounds described herein include, but are not limited to, those wherein $A^1$, for example, is $-OR^a$ or $-C(O)O(R^a)$. Certain compounds described herein include, but are not limited to, those wherein $A^1$ is $-OR^a$. Certain compounds described herein include, but are not limited to, those wherein $A^1$ is $-C(O)O(R^a)$. Yet other compounds described herein include, but are not limited to, those wherein $A^1$, for example, is $G^{1a}$. $R^a$ and $G^{1a}$ are as described in the Summary and herein below. $R^a$, at each occurrence, for example, is independently hydrogen, alkyl (e.g. $C_1$-$C_4$ alkyl such as, but not limited to, methyl, ethyl, tert-butyl), or haloalkyl. In certain embodiments, $R^a$ is hydrogen. Thus, included but not limited to, are compounds wherein $A^1$ is $-OH$. $G^{1a}$, for example, is azetidinyl, pyrrolidinyl, piperidinyl, piperazinyl, tetrahydrofuranyl, tetrahydropyranyl, or morpholinyl, each of which is substituted as described in the Summary and herein. In certain embodiments, $G^{1a}$, for example, is azetidinyl or pyrrolidinyl, each of which is substituted as described in the Summary and herein. In certain embodiments, each $G^{1a}$ is substituted with a group selected from $-OH$, hydroxyalkyl (e.g. 1-hydroxy-1-methylethyl) group, or $-C(O)O(alkyl)$, and each $G^{1a}$ is optionally further substituted with one or two substituents independently selected from the group consisting of alkyl (e.g. $C_1$-$C_4$ alkyl such as, but not limited to methyl, ethyl) and haloalkyl (e.g. trifluoromethyl).

In conjunction with any above or below embodiments, $A^2$ is as described in the Summary and herein below. $A^2$, for example, is $-OR^a$ or $-C(O)O(R^a)$. In certain embodiments, $A^2$, for example, is $-OR^a$. In certain embodiments, $A^2$, for example, is $-C(O)O(R^a)$. $R^a$ has values as described in the Summary and in the preceding paragraph. In certain embodiments, $A^2$ is $-OH$.

In conjunction with any above or below embodiments, $R^y$ has values as generally described in the Summary and herein. In certain embodiments, each occurrence of $R^y$, if present, is independently alkyl (e.g. $C_1$-$C_4$ alkyl such as, but not limited to, methyl), —CN, haloalkyl (e.g. trifluoromethyl and the like), —OH, —O($C_1$-$C_4$ alkyl), or halogen. In other embodiments, $R^y$, at each occurrence, is independently methyl, fluoro, chloro, bromo, —CN, or trifluoromethyl. In yet other embodiments, $R^y$, for example, is haloalkyl (includes, but not limited thereto, trifluoromethyl).

Ring A of formula (I) is described generally in the Summary and in embodiments herein.

In certain embodiments, ring A is formula (a)

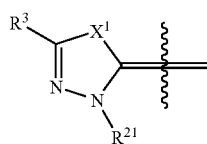

(a)

wherein $R^3$, $X^1$, and $R^{21}$ are as described in the Summary and in embodiments herein.

Examples of compounds include, but are not limited to, those wherein $X^1$ is S.

In conjunction with any of the embodiments herein above and below, examples of $R^3$ include, but are not limited to, alkyl (e.g. $C_1$-$C_4$ alkyl such as, but not limited to, methyl, isopropyl, tert-butyl), alkenyl, alkynyl, haloalkyl (e.g. 2,2,2-trifluoro-1,1-dimethylethyl), or $G^3$ (e.g. optionally substituted $C_3$-$C_6$ cycloalkyl). Particular examples of $R^3$ include, but are not limited to, $C_1$-$C_4$ alkyl (such as, but not limited to, methyl, isopropyl, tert-butyl), alkynyl (e.g. 1,1-dimethyl-prop-2-ynyl), haloalkyl (e.g. 2,2,2-trifluoro-1,1-dimethyl-ethyl and the like), and optionally substituted $C_3$-$C_6$ cycloalkyl (e.g. cyclopropyl, and cyclobutyl, wherein the cyclopropyl and cyclobutyl are each independently unsubstituted or substituted as described in the Summary and herein below). Examples of the optional substituents of cycloalkyl include, but are not limited to, alkyl (e.g. $C_1$-$C_4$ alkyl such as, but not limited to, methyl, ethyl), haloalkyl (e.g. trifluoromethyl), and halogen (e.g. F, Cl, Br).

In other embodiments, ring A is formula (b)

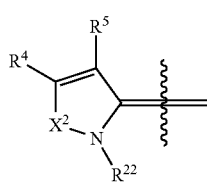

(b)

wherein $R^4$, $R^5$, $R^{22}$, and $X^2$ are as defined in the Summary and in embodiments herein.

In conjunction with any of the embodiments herein above and below, examples of $R^4$ include, but are not limited to, alkyl (e.g. $C_1$-$C_4$ alkyl such as, but not limited to, tert-butyl) or optionally substituted $C_3$-$C_6$ cycloalkyl. For example, $R^4$ is tert-butyl or optionally substituted cyclopropyl. In certain embodiments, $R^4$ is tert-butyl.

In conjunction with any of the embodiments herein above and below, $R^5$, for example, is hydrogen, alkyl, or halogen. In certain embodiments, $R^5$ is hydrogen or halogen (e.g. Br). In certain embodiments, $R^5$ is hydrogen.

In certain embodiments, $X^2$ is O.

In yet other embodiments, $X^2$ is N($R^{10}$) wherein $R^{10}$ is as disclosed in the Summary and herein. For example, in conjunction with any of the above or below embodiments, $R^{10}$ is $C_1$-$C_4$ alkyl such as, but not limited to, methyl.

Yet other embodiments direct to compounds of formula (I) wherein ring A is formula (c)

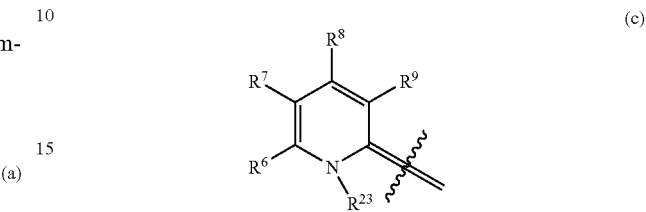

(c)

wherein $R^6$, $R^7$, $R^8$, $R^9$ and $R^{23}$ are as defined in the Summary and embodiments herein.

$R^6$ and $R^9$ are, for example, hydrogen.

$R^7$ and $R^8$ are, for example, each independently hydrogen or $C_1$-$C_4$ alkyl such as, but not limited to, methyl, ethyl, tert-butyl, and the like.

Yet still other embodiments provide compounds wherein ring A is formula (d)

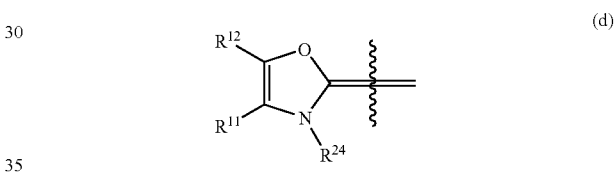

(d)

wherein $R^{11}$, $R^{12}$, and $R^{24}$ are as defined in the Summary.

In conjunction with any one of the above or below embodiments, $R^{11}$ and $R^{12}$, for example, are each independently hydrogen, halogen, or alkyl (e.g. $C_1$-$C_4$ alkyl). For example, $R^{12}$ is alkyl such as, but not limited to, tert-butyl, and $R^{11}$ is hydrogen.

$R^{21}$, $R^{22}$, $R^{23}$, and $R^{24}$ in formula (a), (b), (c), and (d) are as described generally in the Summary and in embodiments herein. For example, in certain embodiments, $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), —$(CR^{2a}R^{2b})_{q4}$—OH, —$(CR^{2a}R^{2b})_{q4}$—O-alkyl (such as, but not limited to, 3-methoxypropyl), —$(CR^{2a}R^{2b})_{q4}$—O-haloalkyl, or —$(CR^{2a}R^{2b})_{q5}$-$G^{2b}$ wherein $R^{2a}$, $R^{2b}$, q4, q5, and $G^{2b}$ are as described in the Summary and in embodiments herein. In certain embodiments, $R^{2a}$ and $R^{2b}$, are each independently hydrogen or $C_1$-$C_4$ alkyl. In certain embodiments, q5 is 1. $G^{2b}$, for example, is an optionally substituted monocyclic cycloalkyl such as, but not limited to, cyclopropyl, cyclobutyl, cyclopentyl, each of which is optionally substituted as described in the Summary.

It is appreciated that compounds of formula (I), (I-ii), and (I-iii) with combinations of the above embodiments, including particular, more particular and preferred embodiments are contemplated.

Accordingly, one aspect relates to a group of compounds of formula (I), (I-i), (I-ii) and (I-iii) wherein Ring A is formula (a) and $X^1$ is S.

Another aspect provides a group of compounds of formula (I), (I-i), (I-ii) and (I-iii) wherein Ring A is formula (a), $X^1$ is S, and $R^3$ is $C_1$-$C_4$ alkyl (such as, but not limited to, methyl, isopropyl, tert-butyl), alkynyl (e.g. 1,1-dimethylprop-2-ynyl), haloalkyl (e.g. 2,2,2-trifluoro-1,1-dimethylethyl and the like), and optionally substituted $C_3$-$C_6$ cycloalkyl (e.g. cyclopropyl, and cyclobutyl, wherein each is independently unsubstituted or substituted as described in the Summary and embodiments herein above).

Another aspect provides a group of compounds of formula (I), (I-i), (I-ii) and (I-iii) wherein Ring A is formula (b) and $X^2$ is O.

Yet another aspect provides a group of compounds of formula (I), (I-i), (I-ii) and (I-iii) wherein Ring A is formula (b) and $X^2$ is $N(R^{10})$.

Yet another aspect provides a group of compounds of formula (I), (I-i), (I-ii) and (I-iii) wherein Ring A is formula (b), $X^2$ is $N(R^{10})$, $R^4$ is alkyl or optionally substituted $C_3$-$C_6$ cycloalkyl, $R^5$ is hydrogen, alkyl, or halogen, and $R^{10}$ is as described in the Summary and embodiments herein. In certain embodiments, $R^{10}$ is $C_1$-$C_4$ alkyl such as, but not limited to, methyl. In certain embodiments, $R^4$ is tert-butyl or optionally substituted cyclopropyl. In certain embodiments, $R^4$ is tert-butyl. In certain embodiments, $R^5$ is hydrogen.

A further aspect provides a group of compounds of formula (I), (I-i), (I-ii) and (I-iii) wherein Ring A is formula (c), $R^6$ and $R^9$ are hydrogen, $R^7$ and $R^8$ are each independently hydrogen or $C_1$-$C_4$ alkyl.

Yet a further aspect provides a group of compounds of formula (I), (I-i), (I-ii) and (I-iii) wherein Ring A is formula (d), $R^{11}$ and $R^{12}$, for example, are each independently hydrogen, halogen, or alkyl.

Within each group of compounds described herein above, $R^1$, $R^{21}$, $R^{22}$, $R^{23}$, $R^{24}$, $R^3$, $R^4$, $R^5$, $R^6$, $R^7$, $R^8$, $R^9$, $R^{10}$, $R^{11}$, $R^{12}$, $X^1$, $X^2$, $R^x$, $R^y$, and $z$ have values as disclosed in the Summary and the Detailed Description.

For example, of each groups of compounds of formula (I), (I-i), (I-ii), and (I-iii), as described in the preceding paragraphs, examples of a subgroup include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$ wherein $R^{2a}$, $R^{2b}$, q4, q5, and $G^{2b}$ are as described in the Summary and Detailed Description sections.

Examples of another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, and $R^x$ is $-(CR^{1a}R^{1b})_{q1}-A^1$ or alkenyl substituted with one $A^2$ group, wherein $R^{1a}$, $R^{1b}$, q1, $A^1$, $A^2$, $R^{2a}$, $R^{2b}$, q4, q5, and $G^{2b}$ are as described in the Summary and Detailed Description sections.

Examples of another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$ or alkenyl substituted with one $A^2$ group, $A^1$ is $-OR^a$, $-C(O)OR^a$, or $G^{1a}$; $A^2$ is $-OR^a$; wherein $R^{1a}$, $R^{1b}$, $R^a$, q1, $R^{2a}$, $R^{2b}$, q4, q5, $G^{1a}$, and $G^{2b}$ are as described in the Summary and Detailed Description sections.

Examples of yet another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$, and $A^1$ is $G^{1a}$, wherein $R^{1a}$, $R^{1b}$, q1, $G^{1a}$, $R^{2a}$, $R^{2b}$, q4, q5, and $G^{2b}$ are as described in the Summary and Detailed Description sections.

Examples of yet another subgroup of compounds of formula (I), (I-i), (I-ii), or (I-iii), include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$, $A^1$ is $G^{1a}$, and $G^{1a}$ is azetidinyl, piperidinyl, piperazinyl, tetrahydrofuranyl, tetrahydropyranyl, or morpholinyl, each of which is substituted as described herein above, and $R^{1a}$, $R^{1b}$, q1, $R^{2a}$, $R^{2b}$, q4, q5, and $G^{2b}$ are as described in the Summary and Detailed Description sections.

Examples of yet another subgroup of compounds of formula (I), (I-i), (I-ii), or (I-iii), include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$, and $A^1$ is $-OR^a$ or $-C(O)O(R^a)$, and $R^a$, $R^{1a}$, $R^{1b}$, q1, $R^{2a}$, $R^{2b}$, q4, q5, and $G^{2b}$ are as described in the Summary and Detailed Description sections. $R^a$, at each occurrence, for example, is independently hydrogen, alkyl (e.g. $C_1$-$C_4$ alkyl such as, but not limited to, methyl, ethyl, tert-butyl), or haloalkyl.

Examples of yet another subgroup of compounds of formula (I), (I-i), (I-ii), or (I-iii), include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$, and $A^1$ is $-OR^a$, and $R^a$, $R^{1a}$, $R^{1b}$, q1, $R^{2a}$, $R^{2b}$, q4, q5, and $G^{2b}$ are as described in the Summary and Detailed Description sections. In certain embodiments, $R^a$, for example, is hydrogen.

Examples of yet another subgroup of compounds of formula (I), (I-i), (I-ii), or (I-iii), include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$, $R^x$ is $-(CR^{1a}R^{1b})_{q1}-A^1$, and $A^1$ is $-C(O)O(R^a)$, and $R^a$, $R^{1a}$, $R^{1b}$, q1, $R^{2a}$, $R^{2b}$, q4, q5, and $G^{2b}$ are as described in the Summary and Detailed Description sections. In certain embodiments, $R^a$, for example, is alkyl (e.g. $C_1$-$C_4$ alkyl such as, but not limited to, methyl, ethyl, tert-butyl), or haloalkyl.

Examples of yet another subgroup of compounds of formula (I), (I-i), (I-ii), and (I-iii), include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}$ $R^{2b})_{q5}$-$G^{2b}$, and $R^x$ is alkenyl (such as, but not limited to, 3-methylbut-1-enyl) substituted with one $A^2$ group, wherein $A^2$, $R^{2a}$, $R^{2b}$, q4, q5, and $G^{2b}$ are as described in the Summary and Detailed Description sections.

Examples of yet another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), —$(CR^{2a}R^{2b})_{q4}$—OH, —$(CR^{2a}R^{2b})_{q4}$—O-alkyl (such as, but not limited to, 3-methoxypropyl), —$(CR^{2a}R^{2b})_{q4}$—O-haloalkyl, or —$(CR^{2a}R^{2b})_{q5}$-$G^{2b}$, $R^x$ is alkenyl (such as, but not limited to, 3-methylbut-1-enyl) substituted with one $A^2$ group, and $A^2$ is —$OR^a$, wherein $R^a$, $R^{2a}$, $R^{2b}$, q4, q5, and $G^{2b}$ are as described in the Summary and Detailed Description sections. In certain embodiments, $R^a$, for example, is hydrogen.

Included, but not limited thereto, are compounds of formula (I) wherein $R^1$ is an aryl group substituted by one $R^x$ group and optionally further substituted with 1 or 2 $R^y$ groups; wherein $R^x$ is —$(CR^{1a}R^{1b})_{q1}$-$A^1$ or alkenyl substituted with one $A^2$ group; and each $R^y$, if present, is independently alkyl (e.g. $C_1$-$C_4$ alkyl such as, but not limited to, methyl), —CN, haloalkyl, —OH, —O($C_1$-$C_4$ alkyl), or halogen. In certain embodiments, $A^1$ is —$OR^a$, —$C(O)O(R^a)$, or $G^{1a}$. Certain compounds described herein include, but are not limited to, those wherein $A^1$ is —$OR^a$. Certain compounds described herein include, but are not limited to, those wherein $A^1$ is —$C(O)O(R^a)$. Yet other compounds described herein include, but are not limited to, those wherein $A^1$, for example, is $G^{1a}$. $R^a$ and $G^{1a}$ are as described in the Summary and herein. $R^a$, at each occurrence, for example, is independently hydrogen, alkyl (e.g. $C_1$-$C_4$ alkyl such as, but not limited to, methyl, ethyl, tert-butyl), or haloalkyl. In certain embodiments, $R^a$ is hydrogen. Thus, included but not limited to, are compounds wherein $A^1$ is —OH. $G^{1a}$, for example, is azetidinyl, pyrrolidinyl, piperidinyl, piperazinyl, tetrahydrofuranyl, tetrahydropyranyl, or morpholinyl, each of which is substituted as described in the Summary and herein. In certain embodiments, $G^{1a}$, for example, is azetidinyl or pyrrolidinyl, each of which is substituted as described in the Summary and herein. In certain embodiments, each $G^{1a}$ is substituted with a group selected from —OH, hydroxyalkyl (e.g. 1-hydroxy-1-methylethyl) group, or —C(O)O(alkyl), and each $G^{1a}$ is optionally further substituted with one or two substituents selected from the group consisting of alkyl (e.g. $C_1$-$C_4$ alkyl such as, but not limited to methyl, ethyl) and haloalkyl (e.g. trifluoromethyl). $A^2$, for example, is —$OR^a$ or —$C(O)O(R^a)$. In certain embodiments, $A^2$, for example, is —$OR^a$. In certain embodiments, $A^2$, for example, is —$C(O)O(R^a)$. $R^a$ has values as described in the Summary and in the preceding paragraphs. In certain embodiments, $A^2$ is —OH.

Specific embodiments of compounds contemplated include, but are not limited to:

N-[(3E)-2-butyl-5-tert-butyl-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-pentyl-1,2-dihydro-3H-pyrazol-3-ylidene]-2-(3-hydroxy-3-methylbutyl)-5-(trifluoromethyl)benzamide;

N-[(3E)-5-tert-butyl-2-(cyclopropylmethyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclopropylmethyl)-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-propyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclobutylmethyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclobutylmethyl)-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-propyl-1,2-dihydro-3H-pyrazol-3-ylidene]-2-(3-hydroxy-3-methylbutyl)-5-(trifluoromethyl)benzamide;

N-[(3E)-5-tert-butyl-2-(cyclopropylmethyl)-1-methyl-1,2-dihydro-3H-pyrazol-3-ylidene]-2-[(3-hydroxyazetidin-1-yl)methyl]-5-(trifluoromethyl)benzamide;

N-[(3E)-5-tert-butyl-2-(cyclopropylmethyl)-1-methyl-1,2-dihydro-3H-pyrazol-3-ylidene]-2-[(3-hydroxy-3-methylazetidin-1-yl)methyl]-5-(trifluoromethyl)benzamide;

ethyl 3-[2-({[(3E)-2-butyl-5-tert-butyl-1-methyl-1,2-dihydro-3H-pyrazol-3-ylidene]amino}carbonyl)-4-(trifluoromethyl)phenyl]propanoate;

N-[(3E)-2-butyl-5-tert-butyl-1-methyl-1,2-dihydro-3H-pyrazol-3-ylidene]-2-[(3-hydroxy-3-methylazetidin-1-yl)methyl]-5-(trifluoromethyl)benzamide;

N-[(3E)-5-tert-butyl-5-tert-butyl-1-methyl-1,2-dihydro-3H-pyrazol-3-ylidene]-2-{[(3R)-3-hydroxypyrrolidin-1-yl]methyl}-5-(trifluoromethyl)benzamide;

N-[(3E)-5-tert-butyl-2-(3-methoxypropyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(3-methoxypropyl)-1-methyl-1,2-dihydro-3H-pyrazol-3-ylidene]-2-(3-hydroxy-3-methylbutyl)-5-(trifluoromethyl)benzamide; and N-[(2Z)-3-butyl-5-tert-butyl-1,3,4-thiadiazol-2(3H)-ylidene]-2-[(3-hydroxyazetidin-1-yl)methyl]-5-(trifluoromethyl)benzamide;

N-[(2Z)-3-butyl-5-tert-butyl-1,3,4-thiadiazol-2(3H)-ylidene]-2-[(3-hydroxy-3-methylazetidin-1-yl)methyl]-5-(trifluoromethyl)benzamide;

N-[(2Z)-3-butyl-5-tert-butyl-1,3,4-thiadiazol-2(3H)-ylidene]-2-{[(3S)-3-hydroxypyrrolidin-1-yl]methyl}-5-(trifluoromethyl)benzamide;

N-[(2Z)-3-butyl-5-tert-butyl-1,3,4-thiadiazol-2(3H)-ylidene]-2-{[(3R)-3-hydroxypyrrolidin-1-yl]methyl}-5-(trifluoromethyl)benzamide;

N-[(2Z)-3-butyl-5-tert-butyl-1,3,4-thiadiazol-2(3H)-ylidene]-2-(hydroxymethyl)-5-(trifluoromethyl)benzamide;

methyl 1-[2-({[(2Z)-3-butyl-5-tert-butyl-1,3,4-thiadiazol-2(3H)-ylidene]amino}carbonyl)-4-(trifluoromethyl)benzyl]azetidine-3-carboxylate;

N-[(2Z)-3-butyl-5-tert-butyl-1,3,4-thiadiazol-2(3H)-ylidene]-2-{[3-(1-hydroxy-1-methylethyl)azetidin-1-yl]methyl}-5-(trifluoromethyl)benzamide;

tert-butyl[2-({[(3E)-2-butyl-5-tert-butyl-1-methyl-1,2-dihydro-3H-pyrazol-3-ylidene]amino}carbonyl)-4-(trifluoromethyl)phenyl]acetate;

N-[(3E)-2-butyl-5-tert-butyl-1-methyl-1,2-dihydro-3H-pyrazol-3-ylidene]-2-[(3-hydroxyazetidin-1-yl)methyl]-5-(trifluoromethyl)benzamide; and N-[(3E)-2-butyl-5-tert-butyl-1-methyl-1,2-dihydro-3H-pyrazol-3-ylidene]-2-[(2-hydroxy-2-methylpropoxy)methyl]-5-(trifluoromethyl)benzamide;

or pharmaceutically acceptable salts, solvates, or salts of solvates thereof.

Compounds of the present application may exist as stereoisomers wherein, asymmetric or chiral centers are present.

These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein may exhibit the phenomenon of tautomerism.

Though structural representations within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{3}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labeled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physico-chemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

C. BIOLOGICAL DATA (i) In Vitro Methods—$CB_2$ and $CB_1$ Radioligand Binding Assays:

The $CB_1$ and $CB_2$ radioligand binding assays described herein are utilized to ascertain the selectivity of compounds of the present application for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a Top-Count using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (0.01 nM to 10 μM) of displacing ligands. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Certain compounds tested bound to $CB_2$ receptors with $K_i$ of less than about 1,000 nM, for example, less than 400 nM, or less than 200 nM, or less than 100 nM.

TABLE 1

| Example # | human $CB_2$ binding ($K_i$, nM) | rat $CB_2$ binding ($K_i$, nM) |
|---|---|---|
| 1 | 133.19 | 101.84 |
| 2 | 32.22 | 25.00 |
| 3 | 41.67 | 37.16 |
| 4 | 151.05 | 121.31 |
| 5 | 277.02 | 89.58 |
| 6 | 10.94 | 3.29 |
| 7 | 20.80 | 17.16 |
| 8 | 1000.00 | 1000.00 |
| 9 | 30.08 | 24.79 |
| 10 | 185.52 | 107.54 |
| 11 | 53.30 | 32.47 |
| 12 | 141.86 | 176.65 |
| 13 | 1000.00 | 452.58 |
| 14 | 111.00 | 30.63 |
| 15 | 1000.00 | 220.21 |
| 16 | 1.63 | 0.80 |
| 17 | 5.90 | 1.45 |
| 18 | 14.89 | 1.59 |
| 19 | 15.34 | 3.85 |
| 20 | 1.89 | 0.57 |
| 21 | 3.93 | 1.79 |
| 22 | 5.33 | 2.14 |
| 23 | 268.95 | 80.16 |
| 24 | 117.04 | 87.51 |
| 25 | 25.00 | 17.78 |

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. Certain compounds tested for $CB_1$ binding, bound to $CB_1$ receptors with $K_i$ values 10×-1000× higher than the $K_i$ for $CB_2$. These results show that the compounds of the present application preferably bind to $CB_2$ receptors, therefore are selective ligands for the $CB_2$ receptor.

D. METHODS OF USING THE COMPOUNDS

One embodiment provides methods for treating pain (for example, inflammatory pain, osteoarthritis pain, eye pain, lower back pain, post-operative pain, cancer pain, neuropathic pain, nociceptive pain, or combinations thereof) in mammals (including human) in need of such treatment. The methods comprise administering to the mammals therapeutically effective amounts of one or more compounds described herein, or pharmaceutically acceptable salts, solvates, or salts of solvates thereof. The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts, solvates, or salts of solvates thereof, in combination with one or more analgesics (for example, acetaminophen or opioids such as, but not limited to, morphine, oxycodone, or related opioids), or with one or more nonsteroidal anti-inflammatory drug (NSAID); or administered with a combination of one or more analgesics and one or more NSAID. Examples of suitable NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition may optionally include one or more pharmaceutically acceptable carriers.

Another embodiment provides methods for treating disorders selected from the group consisting of inflammatory disorders, immune disorders, neurological disorders, cancers of the immune system, respiratory disorders, and cardiovascular disorders in mammals (including human) in need of such treatment. The methods comprise administering to the mammal therapeutically effective amounts of one or more compounds described herein or pharmaceutically acceptable salts, solvates, or salts of solvates thereof, optionally in the presence of one or more pharmaceutically acceptable carriers.

Yet another embodiment relates to methods for providing neuroprotection in mammals (including human) in need of such treatment. These methods comprise administering to the mammal therapeutically effective amounts of one or more compounds described herein or pharmaceutically acceptable salts, solvates, or salts of solvates thereof, optionally in the presence of one or more pharmaceutically acceptable carriers.

Another embodiment of the present invention provides a method of increasing the therapeutic effectiveness or potency of compounds of the invention by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including, but not limited to, multiple sclerosis, rheumatoid arthritis, systemic lupus, myasthenia gravis, type I diabetes, irritable bowel syndrome, psoriasis, psoriatic arthritis, and hepatitis; and immune related disorders including, but not limited to, tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J.

Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients may be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the present compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds may be administered alone, or in combination (i.e. co-administered) with one or more additional pharmaceutical agents. For example, one or more present compounds or pharmaceutically acceptable salts, solvates, or salts of solvates thereof, may be administered in combination with one or more analgesics (e.g acetaminophen or opioids), or with one or more nonsteroidal anti-inflammatory drug (NSAID), or mixtures thereof Non limiting examples of suitable NSAID include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

Therapeutically effective amounts can be determined by those skilled in the art, and will be adjusted to the requirements of each particular case. Generally, a therapeutically effective amount of a $CB_2$ modulator will range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

E. PHARMACEUTICAL COMPOSITIONS

Pharmaceutical compositions comprising compounds described herein or pharmaceutically acceptable salts, solvates, or salts of solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts, solvates, or salts of solvates thereof, and one or more pharmaceutically acceptable carriers, alone or in combination with one or more analgesics (e.g. acetaminophen or opioids such as, but not limited to, morphine, oxycodone, or related opioids), or in combination with one or more nonsteroidal anti-inflammatory drug (NSAID), or a combination of one or more analgesics and one or more NSAID.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

F. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds may be prepared by a variety of processes well known for the preparation of compounds of this class. For example, the compounds of the invention wherein the groups A, $X^1$, $X^2$, $R^1$, $R^3$, $R^4$, $R^5$, $R^{10}$, $R^{11}$, $R^{12}$, $R^{21}$, $R^{22}$, $R^{24}$, $R^x$, $R^y$, $G^{1a}$, and z have the meanings as set forth in the summary section unless otherwise noted, can be synthesized as shown in Schemes 1-6.

Abbreviations which have been used in the descriptions of the Schemes and the Examples that follow are: AcOH for acetic acid, 9-BBN for 9-borabicylco[3.3.1]nonane, DMAP for 4-(dimethylamino)pyridine, DMF for N,N-dimethylformamide, DMSO for dimethyl sulfoxide, dppf for 1,1'-bis (diphenylphosphino)ferrocene, $Et_2O$ for diethyl ether, EtOH for ethanol, EtOAc for ethyl acetate, $Et_3N$ for triethylamine, MeOH for methanol, OTs for tosylate, OMs for mesylate, and THF for tetrahydrofuran.

Scheme 1

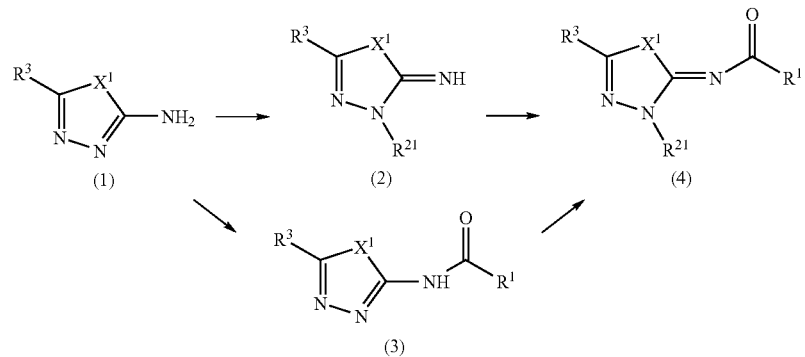

Compounds of formula (I) wherein ring A is formula (a) may be prepared according to the methods illustrated in Scheme 1. Heteroaryl amines of formula (1) can be first reacted with compounds of formula $R^{21}$—$X^{101}$, wherein $X^{101}$ is Cl, Br, I, OTs, or OMs, to form the intermediate (2). This reaction may be performed either neat or in a solvent such as, but not limited to, tetrahydrofuran, acetonitrile, dimethylformamide, dimethylsulfoxide, or dioxane, at about room temperature to about 150° C., and optionally in the presence of a catalyst such as but not limited to tetrabutylammonium iodide or sodium iodide. In certain cases, it may be beneficial to conduct this reaction in the presence of a base such as, but not limited to, triethylamine, potassium carbonate, potassium tert-butoxide, or sodium hydride. The intermediate (2) can be converted to the products (4) by reaction with an appropriate acid chloride or carboxylic acid. For example, intermediate (2) can be reacted with an acid chloride in a solvent such as, but not limited to, tetrahydrofuran, dimethylformamide, or dichloromethane at a temperature from about 25° C. to about 50° C. in the presence of a base such as, but not limited to, triethylamine, diisopropylethylamine, or potassium carbonate, and optionally in the presence of a catalyst such as 4-dimethylaminopyridine. Alternatively, intermediate (2) can be reacted with a carboxylic acid in a solvent such as, but not limited to, tetrahydrofuran or dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N', N'-tetramethyluronium hexafluorophosphate (HATU), O-benzotriazol-1-yl-N,N,N',N'-tetramethyluronium tetrafluoroborate (TBTU), or 1-propanephosphonic acid cyclic anhydride, in the presence or absence of a coupling auxiliary such as, but not limited to, or 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine.

Compounds (1) can also be converted to intermediates (3) by reaction with an acid chloride or carboxylic acid using reaction conditions as described for the conversion of (2) to (4). The intermediate (3) can then be converted to (4) by reaction with $R^{21}$—$X^{101}$, wherein $X^{101}$ is Cl, Br, I, OTs, or OMs, using reaction conditions as described for the transformation of (1) to (2).

Similarly, compounds of general formula (I) wherein Ring A represents formulae (b), (c), and (d) can be prepared from the appropriate heteroaryl or heterocyclic amines using general procedures as illustrated in Scheme 1.

The heteroaryl amines may be obtained from commercial sources or may be prepared using methods well-known to those skilled in the art. For example, heteroaryl amines of formula (1) wherein $X^1$ is sulfur can be prepared using general procedures as illustrated in Scheme 2.

Scheme 2

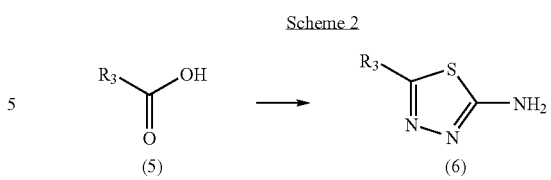

Carboxylic acids of formula (5) can be treated with thiosemicarbazide and phosphorus oxychloride at a temperature of about 90° C., in a solvent such as, but not limited to, dioxane to provide compounds of formula (6).

Compounds of general formula (I) wherein ring A is formula (b) and $X^2$ is $N(R^{10})$ can be synthesized, for example, using the general procedures as outlined in Scheme 3.

Scheme 3

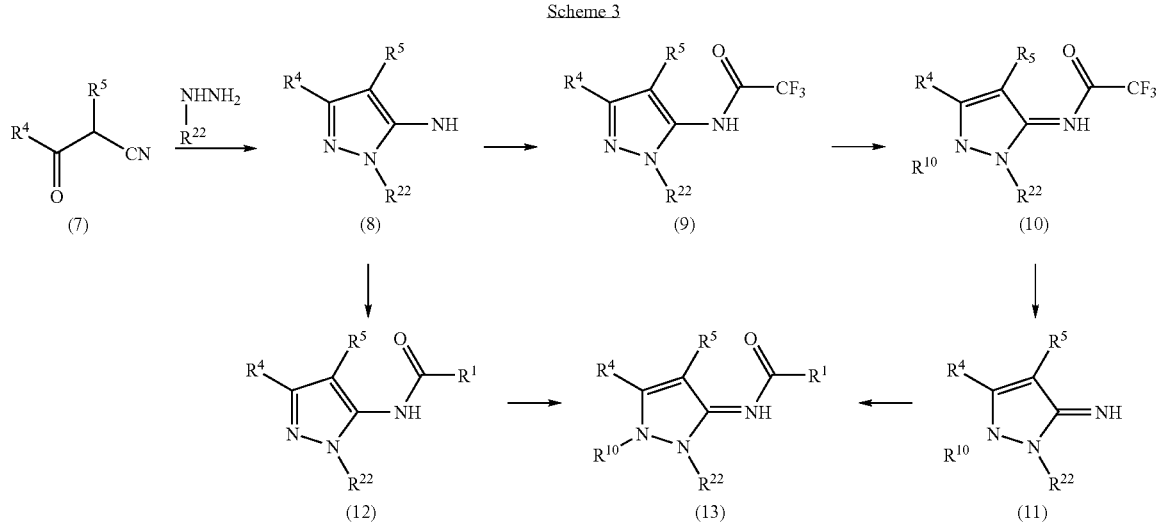

Hydrazines of formula $R^{22}$—$NHNH_2$ can be reacted with ketonitriles (7) in a solvent such as, but not limited to, ethanol, at a temperature of between about 0° C. to about 80° C., to provide intermediates of formula (8). These intermediate aminopyrazoles (8) can be treated with appropriate carboxylic acids or acid chlorides according to the methods outlined in Scheme 1 for the conversion of (2) to (4) to provide pyrazoles (12). Compounds (12) can be converted to (13) by reaction with an appropriate alkylating agent such as, but not limited to, a halide, mesylate, tosylate, triflate, sulfate, or diphenylmethylsulfonium tetrafluoroborate, either neat or in a solvent such as, but not limited to, tetrahydrofuran, toluene, acetonitrile, or dioxane. This reaction may be conducted from about 0° C. to about 150° C. In certain cases the addition of a base may be beneficial. Examples of bases that may be used include triethylamine, diisopropylethylamine, potassium carbonate, sodium hydride, sodium hydroxide, and lithium diisopropylamide.

Alternatively, compounds of formula (8) can be converted to the trifluoroacetamide (9) by reaction with trifluoroacetic anhydride in a solvent such as, but not limited to, methylene chloride and in the presence of a base such as, but not limited to, pyridine or triethylamine. Compounds (9) can be converted to compounds (10) using the conditions described above for the conversion of (12) to (13). Compounds of formula (10) can be converted to (11) by reaction with aqueous potassium or sodium hydroxide with methanol or ethanol as a co-solvent at temperatures from about room temperature to about 70° C. Compounds (11) can be converted to (13) by reaction with the appropriate carboxylic acid or acid chloride according to the conditions of Scheme 1 for the conversion of (2) to (4).

Certain compounds of formula (I) wherein $R^x$ is —CH$_2$-G$^{1a}$ wherein G$^{1a}$ is attached to the methylene group via the nitrogen atom of G$^{1a}$ can be synthesized utilizing general procedures as shown in Scheme 5.

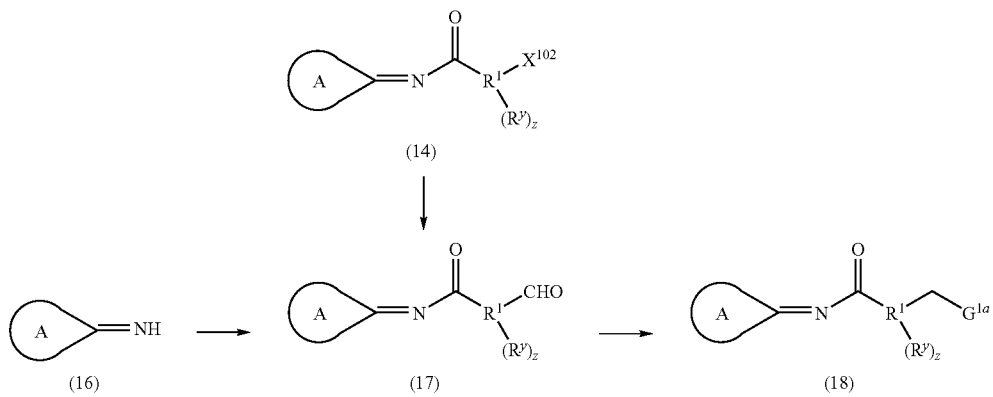

Certain compounds of formula (I) wherein $R^1$ is substituted with —$(CR^{1a}R^{1b})_{q1}$-$A^1$, substituted alkenyl, or substituted alkynyl, can be prepared, for example, using the general procedures as described in Scheme 4.

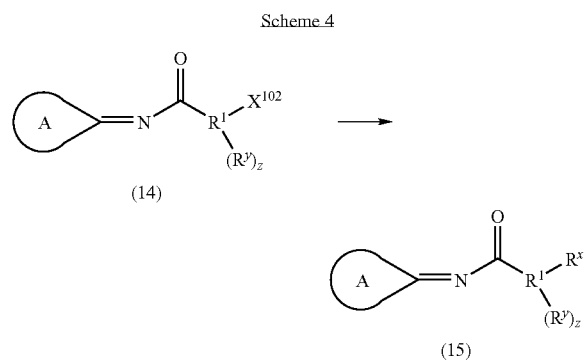

Compounds of formula (15), wherein ring A is as described in formula (I) can be prepared from compounds of formula (14) wherein $X^{102}$ is —Br, triflate, —I, —Cl a boronic acid (or derivative), stannyl, or Zn halide. Reactions that are well-known in the chemical literature for effecting these transformations include the Suzuki, Heck, Stille, Sonogashira, and Negishi reactions. Exemplary reaction conditions can be found in the following references: Negishi, E. A. Handbook of Organopalladium Chemistry for Organic Synthesis; Wiley-Interscience: New York, 2002; Miyaura, N. Cross-Coupling Reactions: A Practical Guide; Springer: New York, 2002. More specifically, compounds of formula (15) wherein $R^x$ is substituted alkenyl, can be prepared using palladium tetrakistriphenyl phosphine as catalyst, cesium fluoride as base, with the corresponding boronic acid or boronic ester, optionally under microwave conditions, at temperatures ranging from about 100° C. to about 140° C. Also, compounds of formula (15) wherein $R^x$ is alkyl or substituted alkyl can be prepared from (14) using palladium acetate, 2-dicyclohexylphosphino-2',6'-dimethoxybiphenyl with the corresponding organic zinc reagent at temperatures ranging from about 50° C. to about 120° C.

Compounds of formula (18) can be prepared from compounds of formula (17) by reductive amination reaction. Reductive amination reactions are well known to those skilled in the art. For example, reaction of compounds (17) with cyclic amines G$^{1a}$-H in a solvent such as, but not limited to, acetonitrile, tetrahydrofuran, dichloromethane, or dichloroethane, in the presence of a reducing agent such as, but not limited to, sodium cyanoborohydride or sodium triacetoxyborohydride, provides compounds (18). The reaction may be conducted in the presence of an acid (e.g., acetic acid).

The intermediates of formula (17) can be prepared from compounds of formula (14) wherein $X^{102}$ is halide by (a) treatment with a metalation agent such as, but not limited to, n-butyl lithium or isopropyl magnesium bromide, and (b) quenching the product of step (a) with dimethylformamide in a solvent such as, but not limited to, tetrahydrofuran, toluene, or dichloromethane at a temperature of about −78° C. to about 0° C. Alternatively, compound of formula (17) can be obtained by coupling of compound of formula (16) with an appropriate acid chloride or carboxylic acid using reaction conditions as described in Scheme 1 for the conversion of (2) to (4).

Compounds of formula (I) wherein ring A is formula (d) may be prepared by the general procedure as shown Scheme 6.

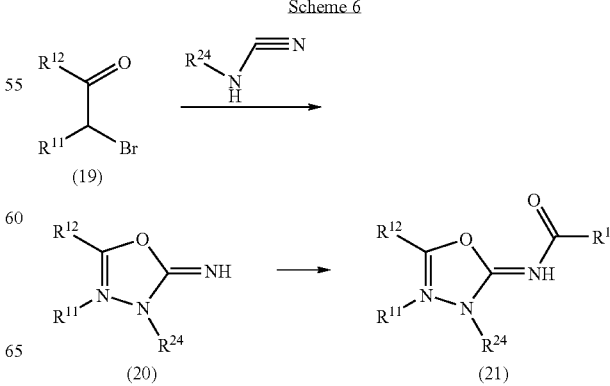

Compounds of formula (19) when treated with compounds of formula R$^{24}$NH—CN in the presence of potassium carbonate, sodium carbonate, or cesium carbonate and in a solvent such as, but not limited to, tetrahydrofuran, dimethoxyethane, dioxane, or methyl ethyl ketone, at a temperature from about 25° C. to about 100° C. are transformed to intermediates of formula (20). Intermediates of formula (20) can be converted to compounds of formula (21) by reaction with an acid chloride or carboxylic acid using reaction conditions as described in Scheme 1.

Compounds of formula (I) wherein A is (b) and X$^2$ is O, and compounds of formula (I) wherein A is (c) may be prepared from isoxazole-3-amines and pyridine-2-amines respectively using synthetic methods that are analogous to those in Schemes 1. The starting isoxazole-3-amines and pyridine-2-amines are either commercially available or can be prepared by known synthetic methods described in the chemical literature.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. G. M. Wuts, Protecting Groups in Organic Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

G. EXAMPLES

Example 1

N-[(3E)-2-butyl-5-tert-butyl-1-methyl-1,2-dihydro-3H-pyrazol-3-ylidene]-2-(3-hydroxy-3-methylbutyl)-5-(trifluoromethyl)benzamide

Example 1A 3-tert-butyl-1-butyl-1H-pyrazol-5-amine

A mixture of n-butylhydrazine oxalate (10 g, 56 mmol) and 4,4-dimethyl-3-oxopentanenitrile (7.0 g, 56 mmol) in ethanol (100 mL) was warmed to 85° C. and was allowed to stir for 3 hours. The mixture was cooled to ambient temperature, and concentrated under reduced pressure. The residue was dissolved in CH$_2$Cl$_2$ (50 mL) and saturated aqueous NaHCO$_3$ (50 mL) w added. The layers were separated and the aqueous layer was extracted with CH$_2$Cl$_2$ (3×10 mL). The combined organic extracts were dried over anhydrous Na$_2$SO$_4$, filtered, and concentrated under reduced pressure to provide the title compound (10 g, 51 mmol, 91% yield) which was used without purification. MS (DCI/NH$_3$) m/z 196 (M+H)$^+$.

Example 1B

N-(3-tert-butyl-1-butyl-1H-pyrazol-5-yl)-2,2,2-trifluoroacetamide

To a solution of Example 1A (10.0 g, 51 mmol) and triethylamine (21.4 mL, 154 mmol) in CH$_2$Cl$_2$ (100 mL) at 0° C. was added 2,2,2-trifluoroacetic anhydride (7.1 mL, 51 mmol) dropwise via syringe pump over 20 min. The ice-bath was removed after the addition was complete and the mixture was stirred at ambient temperature for 1 hour. The mixture was concentrated under reduced pressure and the residue was purified by column chromatography (SiO$_2$, 40% hexanes/EtOAc) to provide the title compound (13.5 g, 46 mmol, 91% yield). MS (DCI/NH$_3$) m/z 292 (M+H)$^+$.

Example 1C (E)-N-(5-tert-butyl-2-butyl-1-methyl-1H-pyrazol-3 (2H)-ylidene)-2,2,2-trifluoroacetamide A mixture of Example 1B (13.5 g, 46.3 mmol) and dimethyl sulfate (13.3 mL, 139 mmol) in toluene (40 mL) was warmed to 90° C. and was allowed to stir for 72 hours. The mixture was cooled to ambient temperature, concentrated under reduced pressure, and the residue was purified by column chromatography (SiO$_2$, 50% hexanes/EtOAc to 100%

EtOAc to 9:1:0.1 EtOAc:MeOH:Et₃N) to give the title compound (7.3 g, 23.7 mmol, 51% yield). MS (DCI/NH₃) m/z 306 (M+H)⁺.

Example 1D 5-tert-butyl-2-butyl-1-methyl-1H-pyrazol-3(2H)-imine

To a solution of Example 1C (7.3 g, 23.7 mmol) in MeOH (35 mL) was added sodium hydroxide (4.8 g, 119 mmol) in water (7 mL). This mixture was warmed to 50° C. for 6 hours then cooled to ambient temperature. The mixture was concentrated under reduced pressure and the residue diluted with CH₂Cl₂ (20 mL) and H₂O (10 mL). The layers were separated and the aqueous layer was extracted with CH₂Cl₂ (3×5 mL). The combined organic extracts were dried over anhydrous Na₂SO₄, filtered, and concentrated under reduced pressure. Recrystallization from methanol and ethyl acetate provided the title compound (4.9 g, 23 mmol, 99% yield). MS (DCI/NH₃) m/z 210 (M+H)⁺.

Example 1E (E)-trimethyl(2-methyl-4-(4,4,5,5-tetramethyl-1,3,2-dioxaborolan-2-yl)but-3-en-2-yloxy)silane To a solution of 3-methyl-3-trimethylsilyloxy-1-butyne (10 mL, 52 mmol) in THF (50 mL) was added pinacolborane (13.2 g, 103 mmol) followed by 9-borabicyclo[3.3.1]nonane dimer (0.62 g, 2.58 mmol). This mixture was warmed to 60° C. and was allowed to stir for 22 hours. The reaction mixture was cooled to 0° C. and was quenched by the slow addition of saturated aqueous NaHCO₃ (10 mL). The mixture was diluted with EtOAc (10 mL) and the layers were separated. The aqueous layer was extracted with EtOAc (3×5 mL) and the combined organics were dried over anhydrous Na₂SO₄, filtered, and concentrated under reduced pressure. A silica gel column was equilibrated with 99% hexanes and 1% of a 10% Et₃N/EtOAc solution. The crude material was then purified via chromatography on this column (SiO₂, 99% hexanes/EtOAc to 80% hexanes/EtOAc) to give the title compound (13.3 g, 46.8 mmol, 91% yield). $^1$H NMR (300 MHz, DMSO-d₆) δ ppm 0.07 (s, 9H) 1.19 (s, 12 H) 1.25 (s, 6H) 5.42 (d, J=18.0 Hz, 1H) 6.53 (d, J=18.0 Hz, 1H).

Example 1F (E)-2-(3-hydroxy-3-methylbut-1-enyl)-5-(trifluoromethyl)benzoic acid A mixture of 2-bromo-5-(trifluoromethyl)benzoic acid (3.0 g, 11.2 mmol), Example 1E (6.3 g, 22.3 mmol), and CsF (5.9 g, 39.0 mmol) in ethylene glycol dimethyl ether (DME, 20 mL) and methanol (10 mL) (in a vacuum tube with a septum) was evacuated and flushed with a nitrogen atmosphere three times. Tetrakis(triphenylphosphine)palladium (0) (1.55 g, 1.34 mmol) was added and the tube was sealed. The mixture was warmed to 90° C. and was allowed to stir for 16 hours. The mixture was then cooled to ambient temperature and was filtered through Celite. The filtrate was concentrated under reduced pressure and the residue was purified via column chromatography (SiO₂, 10% hexanes/EtOAc to 100% EtOAc to 9:1:0.1 EtOAc:MeOH:AcOH) to give the title compound (2.5 g, 9.1 mmol, 82% yield). MS (DCI/NH₃) m/z 292 (M+NH₄)⁺.

Example 1G (E)-N-(5-tert-butyl-2-butyl-1-methyl-1H-pyrazol-3(2H)-ylidene)-2-((E)-3-hydroxy-3-methylbut-1-enyl)-5-(trifluoromethyl)benzamide To a solution of Example 1D (0.50 g, 2.4 mmol) and Example 1F (0.79 g, 2.9 mmol) in THF (10 mL) was added Et₃N (2.0 mL, 14.3 mmol) followed by 2,4,6-tripropyl-1,3,5,2,4,6-trioxatriphosphorinane-2,4,6-trioxide (1.7 mL, 2.9 mmol). This mixture was allowed to stir at ambient temperature for 72 hours. The mixture was quenched with saturated aqueous NaHCO₃ (5 mL) and was diluted with EtOAc (5 mL). The layers were separated and the aqueous layer was extracted with EtOAc (3×3 mL). The combined organics were dried over anhydrous Na₂SO₄, filtered, and concentrated under reduced pressure. The crude material was purified via column chromatography (SiO₂, 50% hexanes/EtOAc to 100% EtOAc to 9:1:0.1 EtOAc:MeOH:Et₃N) to give the title compound (0.23 g, 0.49 mmol, 21% yield). MS (DCI/NH₃) m/z 466 (M+NH₄)⁺.

Example 1H

N-[(3E)-2-butyl-5-tert-butyl-1-methyl-1,2-dihydro-3H-pyrazol-3-ylidene]-2-(3-hydroxy-3-methylbutyl)-5-(trifluoromethyl)benzamide A mixture of Example 1G (0.23 g, 0.49 mmol) and 10% Pd/C (0.053 g, 0.049 mmol) in EtOH (10 mL) was stirred at ambient temperature under an atmosphere of hydrogen (balloon) for 16 hours. The vessel was purged with nitrogen then the mixture was filtered through Celite. The filtrate was concentrated under reduced pressure and purified via column chromatography (SiO₂, 10% hexanes/EtOAc to 100% EtOAc to 9:1:0.1 EtOAc:MeOH:Et₃N) to give the title compound (0.22 g, 0.47 mmol, 95% yield). $^1$H NMR (300 MHz, CD₃OD) δ ppm 0.97 (t, J=7.3 Hz, 3H) 1.20 (s, 6H) 1.32-1.44 (m, 2H) 1.46 (s, 9H) 1.66-1.75 (m, 2 H) 1.76-1.84 (m, 2H) 2.99-3.09 (m, 2H) 3.95 (s, 3H) 4.34 (dd, J=7.1 Hz, 2H) 6.79 (s, 1 H) 7.39-7.45 (m, 1H) 7.53 (dd, J=8.0, 1.5 Hz, 1H) 7.78 (d, J=2.0 Hz, 1H); MS (DCI/NH₃) m/z 468 (M+H)⁻; Elemental Analysis: Calculated for C₂₅H₃₆F₃N₃O₂: C, 63.73; H, 7.79; N, 8.92. Found: C, 63.51; H, 7.43; N, 9.01.

Example 2

N-[(3E)-5-tert-butyl-1-methyl-2-pentyl-1,2-dihydro-3H-pyrazol-3-ylidene]-2-(3-hydroxy-3-methylbutyl)-5-(trifluoromethyl)benzamide

Example 2A pentyl 4-methylbenzenesulfonate

To a solution of pentan-1-ol (9.2 mL, 85 mmol) in CH₂Cl₂ (70 mL) and pyridine (50 mL) was added DMAP (0.52 g, 4.3 mmol) followed by p-toluenesulfonyl chloride (16.2 g, 85 mmol). This mixture was allowed to stir at ambient temperature for 18 hours then quenched with 5% aqueous HCl (20 mL) and diluted with EtOAc (20 mL). The layers were separated and the aqueous layer was extracted with CH₂Cl₂ (3×7 mL). The combined organics were dried over Na₂SO₄, filtered, and concentrated under reduced pressure. The crude material was purified by column chromatography (SiO₂, 75% hexanes in EtOAc) to give the title compound (13.1 g, 53.9 mmol, 63% yield). MS (DCI/NH$_3$) m/z 260 (M+NH$_4$)$^-$.

Example 2B 3-tert-butyl-1-pentyl-1H-pyrazol-5-amine

To a solution of Example 2A (10 g, 41 mmol) in EtOH (85 mL) was added hydrazine hydrate (3.0 mL, 62 mmol). This mixture was warmed to reflux (85° C.) and was allowed to stir for 20 hours. The mixture was cooled to ambient temperature then 4,4-dimethyl-3-oxopentanenitrile (7.8 g, 61.9 mmol) was added and the mixture was again warmed to reflux (85° C.) and was allowed to stir for 4 hours. The mixture was concentrated under reduced pressure and the residue was dissolved in CH$_2$Cl$_2$ (50 mL) and saturated aqueous NaHCO$_3$ (50 mL) was added. The layers were separated and the aqueous layer was extracted with CH$_2$Cl$_2$ (3×10 mL). The combined organics were dried over Na$_2$SO$_4$, filtered, concentrated under reduced pressure and purified via column chromatography (SiO$_2$, 50% hexanes/EtOAc) to provide the title compound (7.6 g, 36.3 mmol, 88% yield). MS (DCI/NH$_3$) m/z 210 (M+H)$^+$.

Example 2C

N-(3-tert-butyl-1-pentyl-1H-pyrazol-5-yl)-2,2,2-trifluoroacetamide

To a solution of Example 2B (7.6 g, 36.3 mmol) and triethylamine (15.2 mL, 109 mmol) in CH$_2$Cl$_2$ (100 mL) at 0° C. was added 2,2,2-trifluoroacetic anhydride (5.05 mL, 36.3 mmol) dropwise via syringe pump over 20 minutes. The ice-bath was removed after the addition was complete and the mixture was stirred at ambient temperature for 1 hour. The mixture was concentrated under reduced pressure and was purified by column chromatography (SiO$_2$, 40% hexanes/EtOAc) to provide the title compound (7.83 g, 25.6 mmol, 71% yield). MS (DCI/NH$_3$) m/z 306 (M+H)$^+$.

Example 2D (E)-N-(5-tert-butyl-1-methyl-2-pentyl-1H-pyrazol-3(2H)-ylidene)-2,2,2-trifluoroacetamide A mixture of Example 2C (7.83 g, 25.6 mmol) and dimethyl sulfate (7.35 mL, 77 mmol) in toluene (10 mL) was warmed to 90° C. and was allowed to stir for 48 hours then was cooled to ambient temperature. The mixture was concentrated under reduced pressure and was purified by column chromatography (SiO$_2$, 50% hexanes/EtOAc to 100% EtOAc to 9:1:0.1 EtOAc:MeOH:Et$_3$N) to give the title compound (4.5 g, 14 mmol, 55% yield). MS (DCI/NH$_3$) m/z 320 (M+H)$^+$.

Example 2E 5-tert-butyl-1-methyl-2-pentyl-1H-pyrazol-3(2H)-imine

To a solution of Example 2D (4.5 g, 14.1 mmol) in MeOH (25 mL) was added sodium hydroxide (2.82 g, 70.5 mmol) in water (5 mL). This mixture was warmed to 50° C., allowed to stir for 4 hours, then cooled to ambient temperature. The mixture was concentrated under reduced pressure and the residue was diluted with CH$_2$Cl$_2$ (20 mL) and H$_2$O (10 mL). The layers were separated and the aqueous layer was extracted with CH$_2$Cl$_2$ (3×5 mL). The combined organics were dried over anhydrous Na$_2$SO$_4$, filtered, and concentrated under reduced pressure to give the crude title compound (3.47 g, 15.5 mmol, 110% yield). MS (DCI/NH$_3$) m/z 224 (M+H)$^+$.

Example 2F (E)-N-(5-tert-butyl-1-methyl-2-pentyl-1H-pyrazol-3(2H)-ylidene)-2-((E)-3-hydroxy-3-methylbut-1-enyl)-5-(trifluoromethyl)benzamide To a solution of Example 2E (0.39 g, 1.73 mmol) and Example 1F (0.57 g, 2.08 mmol) in THF (10 mL) was added Et$_3$N (1.45 mL, 10.4 mmol) followed by 2,4,6-tripropyl-1,3,5,2,4,6-trioxatriphosphorinane-2,4,6-trioxide (1.21 mL, 2.08 mmol). This mixture was allowed to stir at ambient temperature for 20 hours. The mixture was quenched with saturated aqueous NaHCO$_3$ (2 mL) and was diluted with EtOAc (5 mL). The layers were separated and the aqueous layer was extracted with EtOAc (3×3 mL). The combined organics were dried over anhydrous Na$_2$SO$_4$, filtered, and concentrated under reduced pressure. The crude material was purified via column chromatography (SiO$_2$, 50% hexanes/EtOAc to 100% EtOAc to 9:1:0.1 EtOAc:MeOH:Et$_3$N) to give the title compound (0.10 g, 0.21 mmol, 12% yield). MS (DCI/NH$_3$) m/z 480 (M+H)$^+$.

Example 2G

N-[(3E)-5-tert-butyl-1-methyl-2-pentyl-1,2-dihydro-3H-pyrazol-3-ylidene]-2-(3-hydroxy-3-methylbutyl)-5-(trifluoromethyl)benzamide A mixture of Example 2F (0.10 g, 0.21 mmol) and 10% Pd/C (0.022 g, 0.021 mmol) in ethanol (10 mL) was stirred under an atmosphere of hydrogen at ambient temperature for 64 hours. The vessel was purged with nitrogen then the mixture was filtered through Celite. The filtrate was concentrated under reduced pressure and purified via column chromatography (SiO$_2$, 10% hexanes/EtOAc to 100% EtOAc to 9:1:0.1 EtOAc:MeOH:Et$_3$N) to give the title compound (50 mg, 0.10 mmol, 50% yield). $^1$H NMR (300 MHz, CD$_3$OD) δ ppm 0.91 (t, J=7.0 Hz, 3H) 1.20 (s, 6H) 1.27-1.43 (m, 4H) 1.47 (s, 9H) 1.65-1.84 (m, 4 H) 2.98-3.09 (m, 2H) 3.98 (s, 3H) 4.35 (dd, J=7.5 Hz, 2H) 6.82 (s, 1H) 7.44 (d, J=8.1 Hz, 1H) 7.57 (d, J=7.8 Hz, 1H) 7.79 (d, J=1.7 Hz, 1H); MS (DCI/NH$_3$) m/z 482 (M+H)$^+$; Elemental Analysis: calculated for C$_{26}$H$_{38}$F$_3$N$_3$O$_2$: C, 64.84; H, 7.95; N, 8.73. Found: C, 64.94; H, 7.80; N, 8.72.

Example 3

N-[(3E)-5-tert-butyl-2-(cyclopropylmethyl)-1-methyl-1,2-dihydro-3H-pyrazol-3-ylidene]-2-[(1E)-3-hydroxy-3-methylbut-1-enyl]-5-(trifluoromethyl)benzamide Example 3A (cyclopropylmethyl)hydrazine dihydrochloride To a mixture of cyclopropylmethanol (10.1 g, 140 mmol), di-tert-butyl hydrazine-1,2-dicarboxylate (6.50 g, 28.0 mmol) and triphenylphosphine (44.1 g, 168 mmol) in tetrahydrofuran (100 mL) was added di-tert-butyl azodicarboxylate (38.7 g, 168 mmol) in portions. The mixture was stirred at room temperature for 3 hours then diluted with water and ethyl acetate. The organic extract was washed with brine, dried (MgSO$_4$), filtered, and concentrated. The residue was purified by column chromatography using an Analogix® Intelliflash280™ (SiO$_2$, 0-100% hexane in ethyl acetate gradient) to yield di-tert-butyl 1-(cyclopropylmethyl)hydrazine-1,2-dicarboxylate (39 g, 97% yield). $^1$H NMR (300 MHz, CDCl$_3$) δ ppm 0.16-0.27 (m, 2H), 0.40-0.54 (m, 2H), 0.94-1.09 (m, 1H), 1.47 (s, 9H), 1.48 (s, 9H), 3.31 (d, J=6.10 Hz, 2H), 6.38 (s, 1H).

A solution of di-tert-butyl 1-(cyclopropylmethyl)hydrazine-1,2-dicarboxylate (18.0 g, 62.9 mmol) and HCl in dioxane (4 N, 100 mL) was stirred at room temperature overnight. The resulting white solid was filtered, washed with ether (20 mL), and dried to provide the title compound (9.50 g, 59.7 mmol, 95% yield), which was used in the next step. $^1$H NMR (300 MHz, DMSO-d$_6$) δ ppm 0.22-0.34 (m, 2H), 0.46-0.58 (m, 2H), 0.91-1.06 (m, 1H), 2.79 (d, J=7.12 Hz, 2H), 5.91 (s, 5H); MS (DCI) m/z 87 [M+H]$^+$.

Example 3B 3-tert-butyl-1-(cyclopropylmethyl)-1H-pyrazol-5-amine hydrochloride

A mixture of Example 3A (13.5 g, 85 mmol) and 4,4-dimethyl-3-oxopentanenitrile (11.7 g, 93 mmol) in ethanol (100 mL) was heated at reflux for 6 hours. The mixture was cooled to room temperature, and concentrated under reduced pressure. The residue was diluted with ethyl acetate (20 mL). The resulting white precipitate was filtered, washed with ether, and dried to yield 17.5 g (90%) of title compound. $^1$H NMR (300 MHz, DMSO-d$_6$) δ ppm 0.42-0.54 (m, 4H), 1.16-1.27 (m, 1H), 1.28 (s, 9H), 4.38 (d, J=7.12 Hz, 2H), 4.80 (br, 2H), 5.53 (s, 1H), 15.5 (br, 1H); MS (DCI) m/z 194 [M+H]$^+$.

Example 3C

N-(3-tert-butyl-1-(cyclopropylmethyl)-1H-pyrazol-5-yl)-2,2,2-trifluoroacetamide

To a mixture of Example 3B (13 g, 56.6 mmol) and pyridine (18.3 mL, 226 mmol) in dichloroethane (150 mL) was added 2,2,2-trifluoroacetic anhydride (15.73 mL, 113 mmol) dropwise at ambient temperature. The mixture was stirred at ambient temperature for 2 hours, and then water (20 mL) and dichloromethane (20 mL) were added. The organic layer was washed with saturated sodium bicarbonate and brine, and concentrated. The residue was purified by column chromatography using an Analogix® Intelliflash280™ (SiO$_2$, 0-40% hexane in ethyl acetate gradient) to afford the title compound (14.4 g, 88%). $^1$H NMR (300 MHz, DMSO-d$_6$) δ ppm 0.21-0.33 (m, 2H), 0.38-0.49 (m, 2H), 1.04-1.16 (m, 1H), 1.23 (s, 9H), 3.82 (d, J=6.78 Hz, 2H), 6.17 (s, 1H), 11.31 (s, 1H); MS (ESI) m/z 289 [M+H]$^+$.

Example 3D (E)-N-(5-tert-butyl-2-(cyclopropylmethyl)-1-methyl-1H-pyrazol-3(2H)-ylidene)-2,2,2-trifluoroacetamide A mixture of Example 3C (11.6 g, 40 mmol) and dimethyl sulfate (20.2 g, 160 mmol) in toluene (10 mL) was heated at 80° C. for 24 hour. The mixture was concentrated and the residue was purified by column chromatography using an Analogix® Intelliflash280™ (SiO$_2$, eluted with a gradient of 15-100% hexane in solvent B, solvent B: 10:1:0.5 ethyl acetate:methanol:triethylamine) to afford the title compound (8.7 g, 72% yield). $^1$H NMR (300 MHz, DMSO-d$_6$) δ ppm 0.41-0.53 (m, 4H), 1.15-1.27 (m, 1H), 1.38 (s, 9H), 3.98 (s, 3H), 4.20 (d, J=7.12 Hz, 2H), 6.70 (s, 1H); MS (ESI) m/z 304 [M+H]$^+$.

Example 3E 5-tert-butyl-2-(cyclopropylmethyl)-1-methyl-1H-pyrazol-3(2H)-imine

A mixture of 3D (8.7 g, 28.8 mmol) and sodium hydroxide solution (6N, 20 mL) in methanol (100 mL) was stirred at 50° C. overnight, cooled to room temperature, and concentrated under reduced pressure. The residue was extracted with CH$_2$Cl$_2$ (3×100 mL) and the combined organic layers were washed with brine, dried (MgSO$_4$), filtered, and concentrated to afford the title compound (5.3 g, 89% yield) as white solid. $^1$H NMR (300 MHz, DMSO-d$_6$) δ ppm 0.37-0.44 (m, 2H), 0.47-0.54 (m, 2H), 1.07-1.20 (m, 1H), 1.29-1.36 (m, 9H), 3.78 (s, 3H), 4.10 (d, J=6.74 Hz, 2H), 5.60 (s, 1H), 7.19 (s, 1H); MS (+DCI) m/z 208 [M+H]$^+$.

Example 3F (E)-N-(5-tert-butyl-2-(cyclopropylmethyl)-1-methyl-1H-pyrazol-3(2H)-ylidene)-2-bromo-5-(trifluoromethyl)benzamide A solution of 2-bromo-5-(trifluoromethyl)benzoic acid (10 g, 37.2 mmol) in thionyl chloride (44.2 g, 372 mmol) was heated at 90° C. for 2 hours. The reaction mixture was cooled to room temperature, concentrated under reduced pressure, and then azeotroped with toluene to afford 2-bromo-5-(trifluoromethyl)benzoyl chloride, which was used directly in the next step.

To a solution of Example 3E (3.52 g, 17 mmol) in tetrahydrofuran (20 mL) was added sodium hydroxide (2.72 g, 68 mmol) in water (5.00 mL), followed by addition of a solution of 2-bromo-5-(trifluoromethyl)benzoyl chloride (3.85 g, 17 mmol) in tetrahydrofuran (5 mL) dropwise at 0° C. The mixture was stirred at room temperature for 1 hour then diluted with water (20 mL) and ethyl acetate (30 mL). The layers were separated and the organic extract was washed with brine, dried over magnesium sulfate, filtered, and concentrated. The residue was purified by column chromatography using an Analogix® Intelliflash280™ (SiO$_2$, eluted with a gradient of 15-100% hexane in solvent B, solvent B: 10:1:0.5 ethyl acetate:methanol:triethylamine) to afford the title compound (6.3 g, 93%). $^1$H NMR (300 MHz, DMSO-D6) δ ppm 0.41-0.52 (m, 4H) 1.13-1.27 (m, 1H) 1.40 (s, 9H) 3.94 (s, 3H) 4.20 (d, J=6.74 Hz, 2H) 6.83 (s, 1H) 7.54 (dd, J=8.53, 2.18 Hz, 1H) 7.77-7.82 (m, 2H); MS (ESI) m/z 458 [M+H]$^+$.

Example 3G (E)-trimethyl(2-methyl-4-(4,4,5,5-tetramethyl-1,3,2-dioxaborolan-2-yl)but-3-en-2-yloxy)silane To a solution of trimethyl(2-methylbut-3-yn-2-yloxy)silane (1.5 g, 9.6 mmol) in tetrahydrofuran (15 mL) was added 4,4,5,5-tetramethyl-1,3,2-dioxaborolane (2.79 mL, 19.2 mmol), followed by 9-BBN dimer (0.117 g, 0.480 mmol). The mixture was heated at 60° C. for 24 hours, then cooled to ambient temperature and quenched by the careful addition of saturated aqueous ammonium chloride solution. The mixture was extracted with ethyl acetate (2×15 mL). The organics were combined, dried (Na$_2$SO$_4$), filtered, and concentrated under reduced pressure. The residue was purified by column chromatography using an Analogix® Intelliflash280™ (SiO$_2$, eluted with a gradient of 0-60% ethyl acetate in hexanes) to afford the title compound (600 mg, 22% yield). $^1$H NMR (300 MHz, DMSO-d$_6$) δ ppm 0.06-0.08 (m, 9H) 1.19 (s, 12H) 1.25 (s, 6H) 5.41 (d, J=17.85 Hz, 1H) 6.53 (d, J=17.85 Hz, 1H); MS (DCI/NH$_3$) m/z 285 (M+H)$^+$.

Example 3H

N-[(3E)-5-tert-butyl-2-(cyclopropylmethyl)-1-methyl-1,2-dihydro-3H-pyrazol-3-ylidene]-2-[(1E)-3-hydroxy-3-methylbut-1-enyl]-5-(trifluoromethyl) benzamide To a solution of Example 3F (500 mg, 1.091 mmol) and Example 3G (775 mg, 2.73 mmol) in 1,2-dimethoxyethane (1 mL) and methanol (0.500 mL) was added palladium tetrakistriphenyl phosphine (151 mg, 0.131 mmol). This mixture was heated in a microwave oven (Discover Labmate, CEM Corporate) at 110° C. for 10 minutes. The mixture was cooled to room temperature, diluted with water and ethyl acetate, and the layers were separated. The organic extract was dried (Na$_2$SO$_4$), filtered, and concentrated under reduced pressure. The residue was purified by column chromatography using an Analogix® Intelliflash280™ (SiO$_2$, eluted with a gradient of 15-100% hexane in solvent B, solvent B: 10:1:0.5 ethyl acetate:methanol:triethylamine) to afford the title compound (160 mg, 0.345 mmol, 31.6% yield). $^1$H NMR (300 MHz, CDCl$_3$) δ ppm 0.48-0.63 (m, 4H) 1.16-1.23 (m, 1H) 1.43 (s, 6H) 1.45 (s, 9H) 3.83 (s, 3H) 4.22 (d, J=6.74 Hz, 2H) 6.30 (d, J=16.26 Hz, 1H) 7.02 (s, 1H) 7.47-7.61 (m, 3H) 8.14 (s, 1H); MS (DCI/NH$_3$) m/z 464 (M+H)$^-$.

Example 4

N-[(3E)-5-tert-butyl-2-(cyclopropylmethyl)-1-methyl-1,2-dihydro-3H-pyrazol-3-ylidene]-2-(3-hydroxy-3-methylbutyl)-5-(trifluoromethyl)benzamide A mixture of Example 3H (200 mg, 0.431 mmol) and 10% palladium on carbon (18.4 mg) in ethyl acetate (1 mL) and methanol (0.50 mL) was stirred under an atmosphere of hydrogen at room temperature for 4 hours. The mixture was filtered through Celite and the filtrate was concentrated. Purification of the residue by column chromatography using an Analogix® Intelliflash280™ (SiO$_2$, eluted with a gradient of 15-100% hexane in solvent B, solvent B: 10:1:0.5 ethyl acetate:methanol:triethylamine) afforded the title compound (150 mg, 75%). $^1$H NMR (300 MHz, CDCl$_3$) δ ppm 0.50-0.63 (m, 4H) 1.05-1.13 (m, 1H) 1.20 (s, 6H) 1.44 (s, 9H) 1.88-1.94 (m, 2H) 3.09-3.16 (m, 2H) 3.86 (s, 3H) 4.26 (d, J=5.95 Hz, 2H) 7.02 (s, 1H) 7.29 (d, J=7.93 Hz, 1H) 7.47 (d, J=7.93 Hz, 1H) 8.15 (s, 1H). MS (DCI/NH$_3$) m/z 466 (M+H)$^+$. Elemental Analysis: Calculated for C$_{25}$H$_{34}$F$_3$N$_3$O$_2$.0.4CH$_2$Cl$_2$.1.9H$_2$O: C, 57.16; H, 7.29; N, 7.87. Found: C, 57.55; H, 7.40; N, 7.47.

Example 5

N-[(3E)-5-tert-butyl-1-methyl-2-propyl-1,2-dihydro-3H-pyrazol-3-ylidene]-2-[(1E)-3-hydroxy-3-methylbut-1-enyl]-5-(trifluoromethyl)benzamide Example 5A 3-tert-butyl-1-propyl-1H-pyrazol-5-amine A mixture of propylhydrazine oxalate (5.0 g, 30.5 mmol) and 4,4-dimethyl-3-oxopentanenitrile (3.8 g, 30.5 mmol) in 60 mL of absolute ethanol was warmed at 85° C. for 4 hours. The solvent was removed under reduced pressure and the residue was washed with diethyl ether and dried. The residue was diluted with EtOAc, washed with 10% NaHCO$_3$, water, brine, dried with MgSO$_4$, filtered, and concentrated under reduced pressure to afford the title compound (5.3 g, 29 mmol, 96% yield). $^1$H NMR (300 MHz, DMSO-d$_6$) δ ppm 0.82 (t, J=7.5 Hz, 3H), 1.14 (s, 9H), 1.54-1.70 (m, 2H), 3.63-3.75 (m, 2H), 4.89 (s, 2H), 5.10 (s, 1H). MS (ESI$^+$) m/z 182.0 (M+H)$^+$.

Example 5B

N-(3-tert-butyl-1-propyl-1H-pyrazol-5-yl)-2,2,2-trifluoroacetamide

Trifluoroacetic anhydride (1.9 mL, 13.2 mmol) was added to a 0° C. solution of triethylamine (5.5 mL, 39.7 mmol) and Example 5A (2.4 g, 13.2 mmol) in 25 mL of dichloromethane. The mixture was stirred at ambient temperature for 2 hours then concentrated under reduced pressure. The residue was purified by chromatography (solvent A is hexane:EtOAc: triethylamine (3:1:0.2); solvent B is hexane:EtOAc:MeOH: triethylamine (2:2:1:0.2); eluted with a gradient from 100% solvent A to 100% solvent B over 300 mL, then isocratic with solvent B for 1000 mL) to afford the title compound (2.9 g, 10.5 mmol, 79% yield). $^1$H NMR (300 MHz, DMSO-d$_6$) δ ppm 0.80 (t, J=7.5 Hz, 3H), 1.22 (s, 9H), 1.62-1.74 (m, 2H), 3.85 (t, J=7.1 Hz, 2H), 6.15 (s, 1H), 11.31 (s, 1H). MS (DCI/NH$_3$) m/z 278.2 (M+H)$^-$.

Example 5C (E)-N-(5-tert-butyl-1-methyl-2-propyl-1H-pyrazol-3(2H)-ylidene)-2,2,2-trifluoroacetamide A mixture of Example 5B (2.9 g, 10.5 mmol) and dimethyl sulfate (3.0 mL, 31.4 mmol) in 10 ml, of toluene was heated at 90° C. for 72 hours. The reaction mixture was cooled and then concentrated under reduced pressure. Purification by chromatography (solvent A is hexane:EtOAc:triethylamine (1:1:0.2); solvent B is hexane:EtOAc:MeOH:triethylamine (2:2:1:0.2); eluted with a gradient from 100% solvent A to 100% solvent B over 600 mL, then isocratic with solvent B for 600 mL) afforded the title compound (1.5 g, 5.2 mmol, 49% yield). $^1$H NMR (300 MHz, DMSO-d$_6$) δ ppm 0.82 (t, J=7.5 Hz, 3H), 1.37 (s, 9H), 1.60-1.72 (m, 2H), 3.92 (s, 3H), 4.25 (t, J=7.3 Hz, 2H), 6.69 (s, 1H). MS (DCI/NH$_3$) m/z 292.3 (M+H)$^-$.

Example 5D 5-tert-butyl-1-methyl-2-propyl-1H-pyrazol-3(2H)-imine

To a solution of Example 5C (1.0 g, 3.4 mmol) in MeOH (5 mL) was added an aqueous solution of sodium hydroxide (0.7 g, 17.2 mmol, 1 mL). The solution was stirred at 50° C. for 3 hours, cooled to room temperature, then concentrated. The residue was diluted with dichloromethane and water, the aqueous layer was extracted with dichloromethane (3×5 mL). The combined organic extracts were dried over MgSO$_4$, filtered, and concentrated under reduce pressure. Crystallization from MeOH/EtOAc afforded the title compound (0.5 g, 2.6 mmol, 75% yield). $^1$H NMR (300 MHz, DMSO-d$_6$) δ ppm 0.85 (t, J=7.3 Hz, 3H), 1.31 (s, 9H), 1.48-1.69 (m, 2H), 3.68

(s, 3H), 4.09 (t, J=7.3 Hz, 2H), 5.74 (s, 1H), 7.70 (s, 1H). MS (DCI/NH$_3$) m/z 196.1 (M+H)$^+$.

Example 5E

N-[(3E)-5-tert-butyl-1-methyl-2-propyl-1,2-dihydro-3H-pyrazol-3-ylidene]-2-[(1E)-3-hydroxy-3-methylbut-1-enyl]-5-(trifluoromethyl)benzamide To a solution of Example 5D (0.15 g, 0.77 mmol), Example 1F (0.18 g, 0.64 mmol), and triethylamine (0.214 mL, 1.54 mmol) in THF (2.5 mL) was added diethyl cyanophosphonate (0.16 mL, 0.96 mmol) dropwise. The reaction mixture was stirred at ambient temperature for 3 hours then concentrated under reduced pressure. Purification of the residue by chromatography (solvent A is hexane:ethylacetate:triethylamine (1:1:0.1); solvent B is hexane:ethylacetate:methanol:triethylamine (2:2:1:0.2); eluted with a gradient from 100% solvent A to 100% solvent B over 750 mL) afforded the title compound (0.11 g, 0.24 mmol, 38% yield). $^1$H NMR (500 MHz, pyridine-d$_5$) δ ppm 0.81 (t, J=7.5 Hz, 3H), 1.20 (s, 9H), 1.61 (s, 6H), 1.65-1.71 (m, 2H), 3.73 (s, 3H), 4.37 (t, J=7.5 Hz, 2H), 6.76 (d, J=16.2 Hz, 1H), 7.45 (s, 1H), 7.65 (dd, J=8.2, 1.5 Hz, 1H), 7.87 (d, J=8.2 Hz, 1H), 8.48 (d, J=16.2 Hz, 1H), 8.75 (s, 1H). MS (DCI/NH$_3$) m/z 452.4 (M+H)$^+$.

Example 6

N-[(3E)-5-tert-butyl-2-(cyclobutylmethyl)-1-methyl-1,2-dihydro-3H-pyrazol-3-ylidene]-2-[(1E)-3-hydroxy-3-methylbut-1-enyl]-5-(trifluoromethyl)benzamide Example 6A cyclobutylmethyl 4-methylbenzenesulfonate To a solution of cyclobutanemethanol (11.0 mL, 116 mmol) in CH$_2$Cl$_2$ (35 mL) and pyridine (35 mL) was added DMAP (0.71 g, 5.81 mmol) followed by p-toluenesulfonyl chloride (22.1 g, 116 mmol). This mixture was allowed to stir at ambient temperature for 16 hours then was quenched with 5% aqueous HCl (40 mL) and diluted with CH$_2$Cl$_2$ (20 mL). The layers were separated and the aqueous layer was extracted with CH$_2$Cl$_2$ (3×10 mL). The combined organics were dried over Na$_2$SO$_4$, filtered, and concentrated under reduced pressure. The crude material was purified by column chromatography (SiO$_2$, eluted with 75% hexanes in EtOAc) to give the title compound (24.7 g, 103 mmol, 89% yield). MS (DCI/NH$_3$) m/z 258 (M+NH$_4$)$^+$.

Example 6B 3-tert-butyl-1-(cyclobutylmethyl)-1H-pyrazol-5-amine

To a solution of 6A (24.7 g, 103 mmol) in EtOH (130 mL) was added hydrazine hydrate (7.51 mL, 154 mmol). This mixture was warmed to reflux (85° C.) and was allowed to stir for 20 hours. The mixture was cooled to ambient temperature then 4,4-dimethyl-3-oxopentanenitrile (19.3 g, 154 mmol) was added and the mixture was again warmed to reflux (85° C.). The mixture was allowed to stir for 4 hours, cooled to room temperature, and was concentrated under reduced pressure. The residue was dissolved in CH$_2$Cl$_2$ (50 mL) and saturated aqueous NaHCO$_3$ (30 mL) was added. The layers were separated and the aqueous layer was extracted with CH$_2$Cl$_2$ (3×10 mL). The combined organics were dried over Na$_2$SO$_4$, filtered, and concentrated under reduced pressure. The residue was purified by column chromatography (SiO$_2$, eluted with 50% hexanes/EtOAc) to provide the title compound (12.4 g, 59.6 mmol, 58% yield). MS (DCI/NH$_3$) m/z 208 (M+H)$^+$.

Example 6C

N-(3-tert-butyl-1-(cyclobutylmethyl)-1H-pyrazol-5-yl)-2,2,2-trifluoroacetamide

To a solution of Example 6B (12.3 g, 59.5 mmol) and triethylamine (24.9 mL, 179 mmol) in CH$_2$Cl$_2$ (150 mL) at 0° C. was added 2,2,2-trifluoroacetic anhydride (8.3 mL, 59.5 mmol) dropwise via syringe pump over 20 min. The ice-bath was removed after the addition was complete and the mixture was stirred at ambient temperature for 1 hour. The mixture was concentrated under reduced pressure and was purified by column chromatography (SiO$_2$, 40% hexanes/EtOAc) to provide the title compound (16.2 g, 53.4 mmol, 90% yield). MS (DCI/NH$_3$) m/z 304 (M+H)$^+$.

Example 6D (E)-N-(5-tert-butyl-2-(cyclobutylmethyl)-1-methyl-1H-pyrazol-3(2H)-ylidene)-2,2,2-trifluoroacetamide To a solution of Example 6C (16.2 g, 53.4 mmol) in toluene (100 mL) was added methyl trifluoromethanesulfonate (10.1 g, 61.4 mmol). This mixture was warmed to 100° C. and was allowed to stir for 16 hours. The mixture was cooled to ambient temperature then was diluted with water (20 mL) and acetone (200 mL). This solution was allowed to stir for 1 hour then concentrated NH$_4$OH (30 mL) was added. The mixture was stirred for 30 minutes then partially concentrated under reduced pressure. The mixture was diluted with EtOAc (50 mL) and brine (15 mL) and the layers were separated. The aqueous layer was extracted with EtOAc (3×10 mL). The combined organics were dried over anhydrous Na$_2$SO$_4$, filtered, and concentrated under reduced pressure. The residue was purified via column chromatography (SiO$_2$, eluted with a gradient of 50% hexanes/EtOAc to 100% EtOAc to 10% MeOH in EtOAc) to give the title compound (9.75 g, 30.7 mmol, 58% yield). MS (DCI/NH$_3$) m/z 318 (M+H)$^+$.

Example 6E 5-tert-butyl-2-(cyclobutylmethyl)-1-methyl-1H-pyrazol-3(2H)-imine

To a solution of Example 6D (9.75 g, 30.7 mmol) in MeOH (50 mL) was added sodium hydroxide (6.14 g, 154 mmol) in water (10 mL). This mixture was stirred at 50° C. for 4 hours, cooled to ambient temperature, and concentrated under reduced pressure. The residue was diluted with CH$_2$Cl$_2$ (20 mL) and H$_2$O (10 mL). The layers were separated and the aqueous layer was extracted with CH$_2$Cl$_2$ (3×5 mL). The combined organics were dried over anhydrous Na$_2$SO$_4$, filtered, and concentrated under reduced pressure to give the title compound (7.8 g, 35.2 mmol, 115% yield). MS (DCI/NH$_3$) m/z 222 (M+H)$^+$.

Example 6F

N-[(3E)-5-tert-butyl-2-(cyclobutylmethyl)-1-methyl-1,2-dihydro-3H-pyrazol-3-ylidene]-2-[(1E)-3-hydroxy-3-methylbut-1-enyl]-5-(trifluoromethyl)benzamide To a solution of Example 6E (1.0 g, 4.52 mmol) and Example 1F (1.24 g, 4.52 mmol) in THF (15 mL) was added Et₃N (1.57 mL, 11.3 mmol), followed by diethyl cyanophosphonate (1.03 mL, 6.78 mmol). This mixture was allowed to stir at ambient temperature for 2 hours, and concentrated under reduced pressure. The residue was purified via column chromatography (SiO₂, eluted with a gradient of 50% hexanes/EtOAc to 100% EtOAc to 9:1:0.1 EtOAc:MeOH:Et₃N) to give the title compound (1.04 g, 2.18 mmol, 48% yield). ¹H NMR (300 MHz, CDCl₃) δ ppm 1.43 (s, 6H) 1.43 (s, 9H) 1.84-1.96 (m, 4H) 1.99-2.10 (m, 2H) 2.60-2.76 (m, 1H) 3.74 (s, 3H) 4.36 (d, J=7.1 Hz, 2H) 6.31 (d, J=16.3 Hz, 1H) 7.00 (s, 1H) 7.47-7.65 (m, 3H) 8.20 (s, 1H); MS (DCI/NH₃) m/z 478 (M+H)⁺; Elemental Analysis calculated for C₂₆H₃₄F₃N₃O₂.0.3H₂O: C, 64.66; H, 7.22; N, 8.70. Found: C, 64.56; H, 7.11: N, 8.84.

Example 7

N-[(3E)-5-tert-butyl-2-(cyclobutylmethyl)-1-methyl-1,2-dihydro-3H-pyrazol-3-ylidene]-2-(3-hydroxy-3-methylbutyl)-5-(trifluoromethyl)benzamide A mixture of Example 6F (0.82 g, 1.72 mmol) and 10% Pd/C (0.18 g, 0.17 mmol) in ethanol (20 mL) was stirred under an atmosphere of hydrogen (balloon) at ambient temperature for 64 hours. The vessel was purged with nitrogen then the mixture was filtered through Celite. The filtrate was concentrated under reduced pressure and the residue was purified via column chromatography (SiO₂, eluted with a gradient of 10% hexanes/EtOAc to 100% EtOAc to 9:1:0.1 EtOAc:MeOH:Et₃N) to give the title compound (0.50 g, 1.04 mmol, 61% yield). ¹H NMR (300 MHz, CD₃OD) δ ppm 1.20 (s, 6H) 1.46 (s, 9H) 1.76-1.84 (m, 2 H) 1.85-1.96 (m, 4H) 1.98-2.10 (m, 2H) 2.69-2.82 (m, 1H) 2.99-3.09 (m, 2H) 3.92 (s, 3H) 4.41 (d, J=7.5 Hz, 2H) 6.80 (s, 1H) 7.40-7.45 (m, 1H) 7.54 (dd, J=8.3, 1.5 Hz, 1H) 7.80 (d, J=2.0 Hz, 1H); MS (DCI/NH₃) m/z 480 (M+H)⁺; Elemental Analysis calculated for C₂₆H₃₆F₃N₃O₂: C, 65.12; H, 7.57; N, 8.76. Found: C, 64.95; H, 7.39; N, 8.85.

Example 8

N-[(3E)-5-tert-butyl-1-methyl-2-propyl-1,2-dihydro-3H-pyrazol-3-ylidene]-2-(3-hydroxy-3-methylbutyl)-5-(trifluoromethyl)benzamide A mixture of Example 5E (0.25 g, 0.55 mmol) and 10% palladium on carbon (60 mg) in 20 mL of 100% EtOH was stirred under an atmosphere of hydrogen (balloon) for 24 hours. The mixture was filtered through Celite (EtOH wash) and the filtrate concentrated. The residue purified by chromatography (SiO₂, eluted with a gradient from 100% dichloromethane to 10% MeOH in dichloromethane over 600 mL, then isocratic for 300 mL) to afford the title compound (0.15 g, 0.33 mmol, 60% yield). ¹H NMR (300 MHz, CD₃OD) δ ppm 0.95 (t, J=7.3 Hz, 3H), 1.20 (s, 6H), 1.47 (s, 9H), 1.73-1.84 (m, 4H), 2.98-3.07 (m, 2H), 3.96 (s, 3H), 4.27-4.35 (m, 2H), 6.81 (s, 1H), 7.40-7.46 (m, 1H), 7.52-7.58 (m, 1 H), 7.76 (s, 1H). MS (DCI/NH₃) m/z 454.3 (M+H)⁺. Elemental Analysis Calculated for C₂₄H₃₄F₃N₃O₂.1.2H₂O: C, 60.67; H, 7.72; N, 8.84. Found: C, 60.70; H, 7.29; N, 8.50.

Example 9

N-[(3E)-5-tert-butyl-2-(cyclopropylmethyl)-1-methyl-1,2-dihydro-3H-pyrazol-3-ylidene]-2-[(3-hydroxyazetidin-1-yl)methyl]-5-(trifluoromethyl)benzamide Example 9A di-tert-butyl 1-(cyclopropylmethyl)hydrazine-1,2-dicarboxylate To a mixture of cyclopropylmethanol (7.15 ml, 90 mmol), di-tert-butyl hydrazine-1,2-dicarboxylate (6.30 g, 27.1 mmol) and triphenylphosphine (28.5 g, 109 mmol) in THF (100 mL) was added di-tert-butyl azodicarboxylate (25 g, 109 mmol) portion wise at ambient temperature. The mixture was stirred for 2 hours then concentrated. Solid triphenylphosphineoxide was removed by filtration. The filtrate was concentrated and the residue was purified by flash chromatography (silica gel, eluted with a gradient of 5-25% EtOAc in hexane) to provide 27.5 g (96%) of title compound. ¹H NMR (300 MHz, CDCl₃) δ ppm 0.15-0.26 (m, 2H), 0.42-0.54 (m, 2H), 0.91-1.09 (m, 1H), 1.47 (s, 9H), 1.48 (s, 9H), 3.31 (d, J=6.10 Hz, 2H), 6.38 (s, 1H).

Example 9B (cyclopropylmethyl)hydrazine dihydrochloride

A mixture of Example 9A (27.5 g, 96 mmol) and 4 M HCl in dioxane (80 mL) was stirred at ambient temperature for 4 hours. The white solid was collected by filtration (Et₂O wash) and dried to afford 15.3 g (100%) of title compound. ¹H NMR (300 MHz, DMSO-d₆) δ ppm 0.22-0.34 (m, 2H), 0.46-0.58 (m, 2H), 0.91-1.06 (m, 1H), 2.79 (d, J=7.12 Hz, 2 H), 5.91 (s, 5H); MS (DCI) m/z 87 [M+H]⁺.

Example 9C 3-tert-butyl-1-(cyclopropylmethyl)-1H-pyrazol-5-amine hydrochloride

A mixture of Example 9B (13.5 g, 85 mmol) and 4,4-dimethyl-3-oxopentanenitrile (11.69 g, 93 mmol) in ethanol (100 mL) was heated at reflux (oil bath temperature of 90° C.) for 6 hours. The mixture was cooled to room temperature, and concentrated under reduced pressure. The residue was diluted with ethyl acetate (20 mL). The resulting white solid was collected by filtration (Et₂O wash) and dried to provide 17.5 g (90%) of title compound. ¹H NMR (300 MHz, DMSO-d₆) δ ppm 0.42-0.54 (m, 4H), 1.16-1.27 (m, 1H), 1.28 (s, 9H), 4.02 (d, J=7.12 Hz, 2H), 5.53 (s, 1H), 6.91 (s, 2H), 14.05 (s, 1H); MS (DCI) m/z 294 [M+H]⁺.

Example 9D

N-(3-tert-butyl-1-(cyclopropylmethyl)-1H-pyrazol-5-yl)-2,2,2-trifluoroacetamide

To the mixture of Example 9C (13 g, 56.6 mmol) and pyridine (18.31 ml, 226 mmol) in CH₂Cl₂ (150 mL) was added 2,2,2-trifluoroacetic anhydride (15.7 mL, 113 mmol) dropwise at ambient temperature. The mixture was stirred at ambient temperature for 2 hours, and then water (20 mL) and CH₂Cl₂ (20 mL) were added. The layers were separated and the organic extract was washed with saturated aqueous NaHCO$_3$ and brine, and then concentrated. Purification by chromatography (silica gel, eluted with 10-40% EtOAc/Hexanes) afforded 4.35 g (88%) of the title compound. $^1$H NMR (300 MHz, DMSO-d$_6$) δ ppm 0.21-0.33 (m, 2H), 0.38-0.49 (m, 2H), 1.04-1.16 (m, 1H), 1.23 (s, 9H), 3.82 (d, J=6.78 Hz, 2H), 6.17 (s, 1H), 11.31 (s, 1H); MS (ESI) m/z 289 [M+H]$^+$, 287 [M−H].

Example 9E (E)-N-(5-tert-butyl-2-(cyclopropylmethyl)-1-methyl-1H-pyrazol-3(2H)-ylidene)-2,2,2-trifluoroacetamide A mixture of Example 9D (11.6 g, 40 mmol) and dimethyl sulfate (20.2 g, 160 mmol) in toluene (10 mL) was heated at 80° C. for 24 hours. The mixture was cooled to room temperature, and concentrated under pressure. The residue was purified by flash chromatography (silica gel, eluted with a gradient of 10-50% hexane in solvent B, solvent B: 10:1:0.5 ethyl acetate:methanol:triethylamine) to afford 8.7 g (72%) of title compound. $^1$H NMR (300 MHz, DMSO-d$_6$) δ ppm 0.41-0.53 (m, 4H), 1.15-1.27 (m, 1H), 1.38 (s, 9H), 3.98 (s, 3H), 4.20 (d, J=7.12 Hz, 2H), 6.70 (s, 1H); MS (ESI) m/z 304 [M+H]$^+$, 302 [M−H].

Example 9F 5-tert-butyl-2-(cyclopropylmethyl)-1-methyl-1H-pyrazol-3(2H)-imine

A mixture of Example 9E (8.7 g, 28.8 mmol) and 6 N NaOH aqueous (20 mL) in MeOH (100 mL) was stirred at 50° C. overnight, cooled to room temperature, and concentrated under reduced pressure. The residue was diluted with water and extracted with CH$_2$Cl$_2$ (3×100 mL). The combined organic extracts were washed with brine and concentrated to provide 5.3 g (89%) of the title compound. $^1$H NMR (300 MHz, DMSO-d$_6$) δ ppm 0.37-0.44 (m, 2H), 0.47-0.54 (m, 2H), 1.07-1.20 (m, 1H), 1.29-1.36 (m, 9H), 3.78 (s, 3H), 4.10 (d, J=6.74 Hz, 2H), 5.60 (s, 1H), 7.19 (s, 1H); MS (+DCI) m/z 208 [M+H]$^+$.

Example 9G (E)-N-(5-tert-butyl-2-(cyclopropylmethyl)-1-methyl-1H-pyrazol-3(2H)-ylidene)-2-fluoro-5-(trifluoromethyl)benzamide To Example 9F (3.52 g, 17 mmol) in THF (20 mL) was added sodium hydroxide (2.72 g, 68 mmol) in water (5.00 mL) following by addition of 2-bromo-5-(trifluoromethyl)benzoyl chloride (3.85 g, 17 mmol) in THF (5 mL) dropwise at 0° C. The mixture was stirred at room temperature for 1 hour then water (20 mL) and ethyl acetate (30 mL) were added. The organic extract was washed with brine, dried over MgSO$_4$, filtered, and concentrated under reduced pressure. Purification of the residue by flash chromatography (silica gel; eluted with a gradient of 10-50% hexanes in solvent B, solvent B: 10:1:0.5 ethyl acetate:methanol:triethylamine) afforded 6.3 g (93%) of the title compound. $^1$H NMR (300 MHz, DMSO-d$_6$) δ ppm 0.42-0.56 (m, 4H), 1.15-1.29 (m, 1H), 1.42 (m, 9 H), 3.95 (s, 3H), 4.24 (d, J=7.14 Hz, 2H), 6.84 (s, 1H), 7.33-7.43 (m, 1H), 7.70-7.78 (m, 1H), 8.12 (dd, J=6.74, 2.38 Hz, 1H); MS (+DCI) m/z 398 [M+H]$^+$.

Example 9H (E)-N-(5-tert-butyl-2-(cyclopropylmethyl)-1-methyl-1H-pyrazol-3(2H)-ylidene)-2-formyl-5-(trifluoromethyl)benzamide To the solution of isopropylmagnesium bromide (3 mL, 2.97 mmol, 1.0 M solution in THF) was added n-butyllithium (2.4 ml, 5.93 mmol, 2.5 M solution in hexane). The mixture was cooled to −78° C., and then a solution of Example 9G (0.680 g, 1.48 mmol) in THF (2 mL) was added dropwise. The mixture was stirred for 1 hour at −78° C. then DMF (0.460 mL, 5.93 mmol) was added, and the mixture was allowed to warm to room temperature. The mixture was quenched with saturated aqueous NH$_4$Cl and extracted with ethyl acetate. The organic layer was washed with brine and concentrated under reduced pressure. Purification of the residue by chromatography (silica gel, eluted with a gradient of 5-50% hexanes in solvent B, solvent B: 10:1:0.5 ethyl acetate:methanol:triethylamine) afforded the title compound (560 mg, 1.374 mmol, 93% yield). $^1$H NMR (300 MHz, DMSO-d$_6$) δ ppm 0.42-0.52 (m, 4H), 1.24-1.36 (m, 1H), 1.42 (s, 9H), 3.98 (s, 3H), 4.30 (d, J=7.14 Hz, 2H), 6.92 (s, 1H), 7.33-7.43 (m, 1H), 7.70-7.78 (m, 1H), 8.7 (dd, J=6.74, 2.38 Hz, 1H), 10.58 (s, 1 H); MS (ESI) m/z 408 [M+H]$^+$, 406[M−H]$^−$.

Example 9I

N-[(3E)-5-tert-butyl-2-(cyclopropylmethyl)-1-methyl-1,2-dihydro-3H-pyrazol-3-ylidene]-2-[(3-hydroxyazetidin-1-yl)methyl]-5-(trifluoromethyl)benzamide To a mixture of Example 9H (100 mg, 0.245 mmol) and azetidin-3-ol hydrochloride (53.8 mg, 0.491 mmol) in pH 4 buffer solution (4 mL) (acetic acid and sodium acetate in MeOH) was added sodium cyanoborohydride (31 mg, 0.49 mmol) portion wise. The mixture was stirred at ambient temperature for 2 hours then concentrated under reduced pressure. The residue was dissolved in EtOAc and washed with saturated aqueous NaHCO$_3$ and brine. The organic extract was dried over MgSO$_4$, filtered, and concentrated under reduced pressure. Purification of the residue by HPLC on a Waters Symmetry C8 column (25 mm×100 mm, 7 μm particle size) using a gradient of 10% to 100% acetonitrile:10 mM ammonium acetate over 8 min (10 min run time) at a flow rate of 40 mL/min to afford 37.1 mg (32.5%) of the title compound. $^1$H NMR (300 MHz, CDCl$_3$) δ ppm 0.49-0.68 (m, 4H), 1.05-1.19 (m, 1H), 1.48 (s, 9H), 3.94 (s, 3H), 4.02-4.12 (m, 2H), 4.12-4.22 (m, 2H), 4.29 (d, J=7.12 Hz, 2H), 4.49-4.59 (m, 1H), 4.70 (s, 2H), 5.07 (s, 1H), 6.93 (s, 1H), 7.64-7.69 (m, 2H), 8.33 (s, 1H); MS (ESI) m/z 465 [M+H]$^+$, 463[M−H]$^−$.

Example 10

N-[(3E)-5-tert-butyl-2-(cyclopropylmethyl)-1-methyl-1,2-dihydro-3H-pyrazol-3-ylidene]-2-[(3-hydroxy-3-methylazetidin-1-yl)methyl]-5-(trifluoromethyl)benzamide The title compound was prepared in 35% yield using analogous procedure as described in Example 9I, replacing azetidin-3-ol hydrochloride with 3-methylazetidin-3-ol hydrochloride. $^1$H NMR (300 MHz, CDCl$_3$) δ ppm 0.49-0.66 (m, 4H), 1.05-1.18 (m, 1H), 1.45 (s, 9H), 1.51 (s, 3H), 1.92-2.04 (m, 1H), 3.05-3.16 (m, 2H), 3.39 (d, J=8.48 Hz, 2 H), 3.84 (s, 3H), 4.23 (d, J=6.78 Hz, 4H), 7.03 (s, 1H), 7.51-7.57 (m, 1H), 7.62-7.68 (m, 1H), 8.17 (d, J=1.70 Hz, 1H); MS (ESI) m/z 479 [M+H]$^+$, 477[M−H]$^-$.

Example 11 ethyl 3-[2-({[(3E)-2-butyl-5-tert-butyl-1-methyl-1,2-dihydro-3H-pyrazol-3-ylidene]amino}carbonyl)-4-(trifluoromethyl)phenyl]propanoate

Example 11A (E)-2-bromo-N-(5-tert-butyl-2-butyl-1-methyl-1H-pyrazol-3(2H)-ylidene)-5-(trifluoromethyl)benzamide The title compound (57% yield) was prepared and isolated using procedure as described in Example 3F, substituting Example 1D for Example 3E. $^1$H NMR (300 MHz, DMSO-d$_6$) δ ppm 0.89 (t, J=7.34 Hz, 3H) 1.23-1.34 (m, 2H) 1.39 (s, 9H) 1.56-1.68 (m, 2 H) 3.88 (s, 3H) 4.27 (t, J=7.34 Hz, 2H) 6.80 (s, 1H) 7.55 (dd, J=8.73, 1.98 Hz, 1H) 7.80 (d, J=8.33 Hz, 1H) 7.86 (d, J=1.98 Hz, 1H); MS (DCI/NH$_3$) m/z 466 (M+H)$^+$.

Example 11B ethyl 3-[2-({[(3E)-2-butyl-5-tert-butyl-1-methyl-1,2-dihydro-3H-pyrazol-3-ylidene]amino}carbonyl)-4-(trifluoromethyl)phenyl]propanoate To a mixture of Example 11A (400 mg, 0.869 mmol), palladium acetate (19.5 mg, 0.087 mmol), dicyclohexyl(2',6'-dimethoxybiphenyl-2-yl)phosphine (71.3 mg, 0.174 mmol) was added a solution of (3-ethoxy-3-oxopropyl)zinc(II) bromide (4.17 mL, 2.085 mmol) in tetrahydrofuran. This mixture was heated at 65° C. for 12 hours then cooled to room temperature and diluted with water and ethyl acetate. The organic layer was separated, dried (Na$_2$SO$_4$), filtered, and concentrated under reduced pressure. The residue was purified by column chromatography using an Analogix® Intelliflash280™ (SiO$_2$, eluted with a gradient of 15-100% hexanes in solvent B, solvent B: 10:1:0.5 ethyl acetate:methanol:triethylamine) to afford the title compound (410 mg, 0.851 mmol, 98% yield). $^1$H NMR (300 MHz, CDCl$_3$) δ ppm 0.96 (t, J=7.29 Hz, 3H) 1.19-1.23 (m, 3H) 1.37-1.41 (m, 2H) 1.44 (s, 9H) 1.64-1.74 (m, 2H) 2.73-2.78 (m, 2H) 3.40 (t, J=7.46 Hz, 2H) 3.80 (s, 3H) 4.10 (q, J=7.12 Hz, 2 H) 4.25-4.39 (m, 2H) 6.91-7.01 (m, 1H) 7.31-7.33 (m, 1H) 7.48 (dd, J=8.14, 1.36 Hz, 1 H) 8.17 (s, 1H); MS (DCI/NH$_3$) m/z 482 (M+H)$^+$.

Example 12

N-[(3E)-2-butyl-5-tert-butyl-1-methyl-1,2-dihydro-3H-pyrazol-3-ylidene]-2-[(3-hydroxy-3-methylazetidin-1-yl)methyl]-5-(trifluoromethyl)benzamide

Example 12A (E)-N-(5-tert-butyl-2-butyl-1-methyl-1H-pyrazol-3(2H)-ylidene)-2-formyl-5-(trifluoromethyl)benzamide The title compound was prepared as described in Example 9H, substituting Example 9G with Example 11A. LCMS (APCI$^+$) m/z 410 [M+H]$^+$.

Example 12B

N-[(3E)-2-butyl-5-tert-butyl-1-methyl-1,2-dihydro-3H-pyrazol-3-ylidene]-2-[(3-hydroxy-3-methylazetidin-1-yl)methyl]-5-(trifluoromethyl)benzamide The title compound was prepared in 35% yield as described in Example 9I, substituting Example 9H with Example 12A and substituting azetidin-3-ol hydrochloride with 3-methylazetidin-3-ol hydrochloride. $^1$H NMR (300 MHz, CDCl$_3$) δ ppm 0.98 (t, J=7.5 Hz, 3 H), 1.33-1.41 (m, 2H), 1.44 (s, 9H), 1.52 (s, 3H), 1.63-1.76 (m, 2H), 2.99-3.28 (m, 2 H), 3.41 (d, J=6.74 Hz, 2H), 3.49 (s, 1H), 3.78 (s, 3H), 4.29 (t, J=7.54 Hz, 4H), 7.01 (s, 1 H), 7.51-7.57 (m, 1H), 7.67 (d, J=7.93 Hz, 1H), 8.24 (s, 1H); MS (ESI) m/z 481 [M+H]$^+$, 479[M−H]$^-$.

Example 13

N-[(3E)-2-butyl-5-tert-butyl-1-methyl-1,2-dihydro-3H-pyrazol-3-ylidene]-2-{[(3R)-3-hydroxypyrrolidin-1-yl]methyl}-5-(trifluoromethyl)benzamide The title compound was prepared in 33% yield as described in Example 9I, substituting Example 12A for Example 9H and replacing azetidin-3-ol hydrochloride with (R)-pyrrolidin-3-ol hydrochloride. $^1$H NMR (500 MHz, pyridine-d$_5$) δ ppm 0.86 (t, J=7.48 Hz, 3H), 1.24 (s, 9H), 1.29-1.36 (m, 2H), 1.61-1.70 (m, 2H), 2.12-2.23 (m, 1H), 2.22-2.36 (m, 1H), 3.22-3.34 (m, 1H), 3.46-3.65 (m, 3H), 3.89 (s, 3H), 4.42-4.49 (m, 2H), 4.70-4.78 (m, 1H), 5.01-5.07 (m, 2H); MS (ESI) m/z 481 [M+H]$^+$, 479[M−H]$^-$.

Example 14

N-[(3E)-5-tert-butyl-2-(3-methoxypropyl)-1-methyl-1,2-dihydro-3H-pyrazol-3-ylidene]-2-[(1E)-3-hydroxy-3-methylbut-1-enyl]-5-(trifluoromethyl)benzamide

Example 14A 3-methoxypropyl 4-methylbenzenesulfonate

To a solution of 3-methoxypropan-1-ol (15.9 mL, 166 mmol) in CH$_2$Cl$_2$ (75 mL) and pyridine (50 mL) was added DMAP (1.0 g, 8.32 mmol), followed by p-toluenesulfonyl chloride (31.7 g, 166 mmol). This mixture was allowed to stir at ambient temperature for 72 hours, then was quenched with 5% aqueous HCl (30 mL). The layers were separated and the aqueous layer was extracted with CH$_2$Cl$_2$ (3×10 mL). The combined organics were dried over Na$_2$SO$_4$, filtered, and concentrated under reduced pressure. The crude material was purified by column chromatography (SiO$_2$, eluted with 75% hexanes in EtOAc) to give the title compound (31 g, 127 mmol, 76% yield). MS (DCI/NH$_3$) m/z 262 (M+NH$_4$).

Example 14B 3-tert-butyl-1-(3-methoxypropyl)-1H-pyrazol-5-amine

To a solution of Example 14A (31 g, 127 mmol) in EtOH (150 mL) was added hydrazine hydrate (8.0 mL, 165 mmol). This mixture was warmed to reflux (85° C.) and was allowed to stir for 20 hours. The mixture was cooled to ambient temperature then 4,4-dimethyl-3-oxopentanenitrile (20.7 g, 165 mmol) was added and the mixture was again warmed to reflux (85° C.) and stirred for 6 hours. The mixture was cooled to room temperature and concentrated under reduced pressure. The residue was dissolved in $CH_2Cl_2$ (50 mL) and saturated, aqueous $NaHCO_3$ (50 mL) was added. The layers were separated and the aqueous layer was extracted with $CH_2Cl_2$ (3×10 mL). The combined organics were dried over $Na_2SO_4$, filtered, concentrated under reduced pressure and purified via column chromatography ($SiO_2$, eluted with a gradient of 50% hexanes in EtOAc to 100% EtOAc to 9:1:0.1 EtOAc:MeOH:$Et_3N$) to provide the title compound (11.4 g, 54.0 mmol, 43% yield). MS (DCI/$NH_3$) m/z 212 (M+H)$^+$.

Example 14C

N-(3-tert-butyl-1-(3-methoxypropyl)-1H-pyrazol-5-yl)-2,2,2-trifluoroacetamide

To a solution of Example 14B (11.4 g, 54.0 mmol) and triethylamine (22.6 mL, 162 mmol) in $CH_2Cl_2$ (130 mL) at 0° C. was added 2,2,2-trifluoroacetic anhydride (8.3 mL, 59.3 mmol) dropwise via syringe pump over 20 min. The ice-bath was removed and the mixture was stirred at ambient temperature for 1 hour. The mixture was concentrated under reduced pressure and was purified by column chromatography ($SiO_2$, eluted with 40% hexanes/EtOAc) to provide the title compound (16.2 g, 52.7 mmol, 98% yield). MS (DCI/$NH_3$) m/z 308 (M+H)$^+$.

Example 14D (E)-N-(5-tert-butyl-2-(3-methoxypropyl)-1-methyl-1H-pyrazol-3(2H)-ylidene)-2,2,2-trifluoroacetamide To a solution of the product of Example 14C (16.2 g, 52.7 mmol) in toluene (100 mL) was added methyl trifluoromethanesufonate (8.7 mL, 79 mmol). This mixture was warmed to 100° C. and was allowed to stir for 16 hours. The mixture was cooled to ambient temperature, diluted with water (30 mL) and acetone (~150 mL) was added until the solution became homogeneous. This solution was allowed to stir for 30 minutes then concentrated $NH_4OH$ (30 mL) was added. The mixture was stirred for 30 minutes and partially concentrated under reduced pressure. The mixture was diluted with EtOAc (30 mL) and brine (15 mL) and the layers were separated. The aqueous layer was extracted with EtOAc (3×10 mL). The combined organics were dried over anhydrous $Na_2SO_4$, filtered, and concentrated under reduced pressure. The residue was purified via column chromatography ($SiO_2$, eluted with a gradient of 50% hexanes/EtOAc to 100% EtOAc to 10% MeOH in EtOAc) to give the title compound (13.1 g, 40.7 mmol, 77% yield). MS (DCI/$NH_3$) m/z 322 (M+H)$^+$.

Example 14E 5-tert-butyl-2-(3-methoxypropyl)-1-methyl-1H-pyrazol-3 (2H)-imine To a solution of the product of Example 14D (13.1 g, 40.7 mmol) in MeOH (60 mL) was added sodium hydroxide (8.1 g, 204 mmol) in water (15 mL). This mixture was stirred at 50° C. for 4 hours, and cooled to ambient temperature. The mixture was concentrated under reduced pressure and then diluted with $CH_2Cl_2$ (20 mL) and $H_2O$ (10 mL). The layers were separated and the aqueous layer was extracted with $CH_2Cl_2$ (3×10 mL). The combined organics were dried over anhydrous $Na_2SO_4$, filtered, and concentrated under reduced pressure to give the title compound (8.67 g, 38.0 mmol, 93% yield). MS (DCI/$NH_3$) m/z 226 (M+H)$^+$.

Example 14F

N-[(3E)-5-tert-butyl-2-(3-methoxypropyl)-1-methyl-1,2-dihydro-3H-pyrazol-3-ylidene]-2-[(1E)-3-hydroxy-3-methylbut-1-enyl]-5-(trifluoromethyl)benzamide To a solution of Example 14E (0.82 g, 3.64 mmol) and Example 1F (1.1 g, 4.0 mmol) in THF (10 mL) was added $Et_3N$ (1.3 mL, 9.1 mmol) followed by diethyl cyanophosphonate (0.83 mL, 5.5 mmol). This mixture was allowed to stir at ambient temperature for 2 hours. The mixture was concentrated under reduced pressure and the residue purified via column chromatography ($SiO_2$, eluted with a gradient of 50% hexanes/EtOAc to 100% EtOAc to 9:1:0.1 EtOAc:MeOH:$Et_3N$) to give the title compound (1.05 g, 2.2 mmol, 60% yield). $^1$H NMR (300 MHz, $CDCl_3$) δ ppm 1.41 (s, 6H) 1.44 (s, 9H) 1.95-2.10 (m, 2H) 2.21-2.28 (m, 1H) 3.26 (s, 3H) 3.37 (t, J=5.6 Hz, 2H) 3.83 (s, 3H) 4.43 (t, J=6.9 Hz, 2H) 6.32 (d, J=15.9 Hz, 1H) 7.01 (s, 1H) 7.47-7.67 (m, 3H) 8.14 (s, 1H); MS (DCI/$NH_3$) m/z 482 (M+H)$^+$.

Example 15

N-[(3E)-5-tert-butyl-2-(3-methoxypropyl)-1-methyl-1,2-dihydro-3H-pyrazol-3-ylidene]-2-(3-hydroxy-3-methylbutyl)-5-(trifluoromethyl)benzamide A mixture of Example 14F (0.90 g, 1.9 mmol) and 10% Pd/C (0.20 g, 0.19 mmol) in ethanol (20 mL) stirred under an atmosphere of hydrogen (balloon) at ambient temperature for 18 hours. After purging the vessel with nitrogen, the mixture was filtered through Celite. The filtrate was concentrated under reduced pressure and the residue purified via column chromatography ($SiO_2$, eluted with a gradient of 10% hexanes/EtOAc to 100% EtOAc to 9:1:0.1 EtOAc:MeOH:$NH_4OH$) to give the title compound (0.50 g, 1.03 mmol, 55% yield). $^1$H NMR (300 MHz, $CDCl_3$) δ ppm 1.21 (s, 6H) 1.42 (s, 9H) 1.91 (dd, J=7.5 Hz, 2H) 1.96-2.06 (m, 2H) 3.14 (dd, J=7.5 Hz, 2H) 3.31 (s, 3H) 3.37 (t, J=5.6 Hz, 2H) 3.81 (s, 3H) 4.31-4.48 (m, 2H) 7.01 (s, 1H) 7.27-7.33 (m, 1H) 7.43-7.53 (m, 1H) 8.20 (s, 1H); MS (DCI/$NH_3$) m/z 484 (M+H)$^+$; Elemental Analysis calculated for $C_{25}H_{36}F_3N_3O_3$: C, 62.09; H, 7.50; N, 8.69. Found; C, 61.91; H, 7.52; N, 8.60.

Example 16

N-[(2Z)-3-butyl-5-tert-butyl-1,3,4-thiadiazol-2(3H)-ylidene]-2-[(3-hydroxyazetidin-1-yl)methyl]-5-(trifluoromethyl)benzamide

Example 16A (E)-N'-(5-tert-butyl-1,3,4-thiadiazol-2-yl)-N,N-dimethylformimidamide A mixture of 5-tert-butyl-1,3,4-thiadiazol-2-amine (Aldrich) (10.0 g, 63.6 mmol) and 1,1-dimethoxy-N,N-dimethylmethanamine (26.3 mL, 197 mmol) in 200 mL of toluene was heated at 100° C. for 12 hours. The mixture was cooled to room temperature and hexane was added. The solid was collected by filtration (hexane wash) to afford the title compound.

Example 16B (E)-5-tert-butyl-3-butyl-2-((dimethylamino)methyleneamino)-1,3,4-thiadiazol-3-ium bromide To a suspension of Example 16A (1.00 g, 4.71 mmol) in toluene (10 mL) was added 1-bromobutane (0.56 mL, 5.18 mmol). The mixture was heated at 100° C. for 12 hours, then cooled to ambient temperature and diluted with hexanes. The solid was collected by filtration (hexane wash) to afford the title compound. $^1$H NMR (300 MHz, DMSO-$d_6$) δ ppm 0.91 (t, J=7.5 Hz, 3H), 1.23-1.36 (m, 2H), 1.39 (s, 9H), 1.70-1.84 (m, 2H), 3.22 (s, 6H), 4.29 (t, J=7.1 Hz, 2H), 8.54 (s, 1H).

Example 16C 5-tert-butyl-3-butyl-1,3,4-thiadiazol-2(3H)-imine

A solution of Example 16B (4 g, 11.45 mmol) in HCl (1 N, 12.6 mL) was heated at 65° C. for 12 hours. The mixture was cooled at room temperature and extracted with ether (2×20 mL). The aqueous phase was neutralized to pH 7 with concentrated ammonia and extracted with ether (2×25 mL). The combined organic extracts were dried over MgSO$_4$, filtered, and concentrated under reduced pressure. The residue was purified by chromatography on SiO$_2$ using an Analogix® Intelliflash280™ (Hexanes-EtOAc: 0-80%) to give the title compound. LC/MS m/z 214 (M+H)$^+$.

Example 16D 2-formyl-5-(trifluoromethyl)benzoic acid

To a solution of n-butyl lithium (56.0 ml, 140 mmol) in tetrahydrofuran (100 mL) at −78° C. was added a solution of 2-bromo-5-(trifluoromethyl)benzoic acid (17.9 g, 66.7 mmol) in tetrahydrofuran (100 mL) over 0.5 hour, at which time the solution turned dark red. After stirring for 1 hour, N,N-dimethylformamide (50 mL, 646 mmol) was added dropwise and the reaction mixture was allowed to warm to room temperature over 6 hours. The mixture was cooled to 0° C. and then a solution of sodium hydroxide (2 N, 120 mL) was added. The mixture was extracted with ether (2×50 mL). The aqueous layer was separated and concentrated hydrochloric acid was added to it until the pH was acidic. The mixture was extracted with ethyl acetate (3×80 mL). The organic extracts were combined, dried with sodium sulfate, filtered, and concentrated. The residue was purified on Analogix® Intelliflash280™ (SiO$_2$, 7-100% solvent A in hexanes; solvent A=3:1:0.1 hexane:ethyl aceate:acetic acid) over 1 hour to obtain the title compound (4.5 g, 20.6 mmol, 31% yield). $^1$H NMR (300 MHz, DMSO-$d_6$) δ ppm 6.78 (br, 1H) 7.93 (d, J=8.48 Hz, 1H) 8.13-8.20 (m, 2H) 8.38 (br, 1H); MS (DCI/NH$_3$) m/z 236 (M+NH$_4$)$^+$.

Example 16E (Z)—N-(5-tert-butyl-3-butyl-1,3,4-thiadiazol-2(3H)-ylidene)-2-formyl-5-(trifluoromethyl)benzamide To a solution of Example 16D (0.365 g, 1.672 mmol) in DMF (10 ml) was added O-benzotriazol-1-yl-N,N,N',N'-tetramethyluronium tetrafluoroborate (0.671 g, 2.090 mmol). The mixture was stirred at room temperature for 10 minutes, and then Example 16C (0.3 g, 1.393 mmol) was added, followed by addition of NEt$_3$ (0.194 mL, 1.393 mmol) to adjust the pH to 5~6. The mixture was stirred at room temperature overnight. The reaction was quenched with water and EtOAc were added, the organic layers were combined, washed with brine, dried over MgSO$_4$, filtered, and concentrated. Purification using an Analogix® Intelliflash280™ (SiO$_2$, 0-100% ethyl acetate in hexanes) yield title compound (0.369 g, 0.892 mmol, 64% yield). $^1$H NMR (400 MHz, CDCl$_3$) δ ppm 1.00 (t, J=7.32 Hz, 3H) 1.36-1.42 (m, 2H) 1.44 (s, 9H) 1.84-1.94 (m, 2H) 4.40 (t, J=7.32 Hz, 2H) 7.80-7.84 (m, 1H) 7.88-7.93 (m, 1H) 8.52 (s, 1H) 10.80 (s, 1H); MS (ESI) m/z 414 (M+H)$^+$, 412 (M−H)$^−$.

Example 16F

N-[(2Z)-3-butyl-5-tert-butyl-1,3,4-thiadiazol-2(3H)-ylidene]-2-[(3-hydroxyazetidin-1-yl)methyl]-5-(trifluoromethyl)benzamide The title compound was prepared and isolated as described in Example 9I, substituting Example 16E for Example 9H in 23% yield. $^1$H NMR (300 MHz, CDCl$_3$) δ ppm 1.00 (t, J=7.34 Hz, 3H) 1.43 (s, 9H) 1.85-1.98 (m, 2H) 2.11-2.62 (m, 4H) 3.26 (d, J=6.74 Hz, 2H) 3.80-3.89 (m, 2H) 4.35-4.45 (m, 3H) 4.46-4.56 (m, 1H) 7.68-7.77 (m, 2H) 8.51 (s, 1H); MS (ESI) m/z 471 (M+H)$^−$, 469 (M−H)$^−$.

Example 17

N-[(2Z)-3-butyl-5-tert-butyl-1,3,4-thiadiazol-2(3H)-ylidene]-2-[(3-hydroxy-3-methylazetidin-1-yl)methyl]-5-(trifluoromethyl)benzamide The title compound was prepared and isolated as described in Example 9I, substituting Example 16E for Example 9H, and substituting 3-methylazetidin-3-ol hydrochloride for azetidin-3-ol hydrochloride in 52.5% yield. $^1$H NMR (300 MHz, DMSO-$d_6$) δ ppm 0.94 (t, J=7.34 Hz, 3H) 1.28-1.36 (m, 2H) 1.37 (s, 3H) 1.40 (s, 9H) 1.78-1.89 (m, 2H) 2.89 (d, J=7.14 Hz, 2H) 3.25 (d, J=7.14 Hz, 2H) 4.12 (s, 2H) 4.38 (t, J=7.14 Hz, 2 H) 5.14 (s, 1H) 7.76-7.87 (m, 2H) 8.28 (s, 1H); MS (ESI) m/z 485 (M+H)$^+$, 483 (M−H)$^−$.

Example 18

N-[(2Z)-3-butyl-5-tert-butyl-1,3,4-thiadiazol-2(3H)-ylidene]-2-{[(3S)-3-hydroxypyrrolidin-1-yl]methyl}-5-(trifluoromethyl)benzamide The title compound was prepared and isolated as described in Example 9I, substituting Example 16E for Example 9H, and substituting (S)-pyrrolidin-3-ol for azetidin-3-ol hydrochloride in 45% yield. $^1$H NMR (300 MHz, DMSO-$d_6$) δ ppm 0.93 (t, J=7.34 Hz, 3 H) 1.27-1.37 (m, 2H) 1.40 (s, 9H) 1.47-1.62 (m, 1H) 1.76-1.89 (m, 2H) 1.89-2.03 (m, J=12.69, 6.74 Hz, 1H) 2.33 (dd, J=9.52, 3.57 Hz, 1H) 2.39-2.47 (m, 1H) 2.54-2.73 (m, 2 H) 4.09 (d, J=7.14 Hz, 2H) 4.13-4.20 (m, 1H) 4.37 (t, J=6.94 Hz, 2H) 4.66 (d, J=4.76 Hz, 1H) 7.80-7.89 (m, 2H) 8.22 (s, 1H); MS (ESI) m/z 485 (M+H)$^+$, 483 (M−H)$^−$.

Example 19

N-[(2Z)-3-butyl-5-tert-butyl-1,3,4-thiadiazol-2(3H)-ylidene]-2-{[(3R)-3-hydroxypyrrolidin-1-yl]methyl}-5-(trifluoromethyl)benzamide The title compound was prepared and isolated as described in Example 9I, substituting Example 16E for Example 9H, and substituting (R)-pyrrolidin-3-ol for azetidin-3-ol hydrochloride in 45% yield. $^1$H NMR (300 MHz, DMSO-d$_6$) δ ppm 0.93 (t, J=7.29 Hz, 3 H) 1.28-1.36 (m, 2H) 1.39 (s, 9H) 1.46-1.62 (m, 1H) 1.76-1.89 (m, 2H) 1.90-2.04 (m, 1H) 2.29-2.47 (m, 2H) 2.57-2.73 (m, 2H) 4.09 (d, J=7.80 Hz, 2H) 4.13-4.23 (m, 1H) 4.37 (t, J=7.12 Hz, 2H) 4.69 (d, J=4.41 Hz, 1H) 7.80-7.91 (m, 2H) 8.22 (s, 1H); MS (ESI) m/z 485 (M+H)$^-$, 483 (M−H)$^-$.

Example 20

N-[(2Z)-3-butyl-5-tert-butyl-1,3,4-thiadiazol-2(3H)-ylidene]-2-(hydroxymethyl)-5-(trifluoromethyl)benzamide Example 20 was a by product from example 19. $^1$H NMR (300 MHz, CDCl$_3$) δ ppm 1.00 (t, J=7.29 Hz, 3H) 1.44 (s, 9H) 1.48-1.62 (m, 4H) 1.82-2.00 (m, 2H) 4.44 (t, 2H) 4.83 (s, 1H) 7.53 (d, J=7.80 Hz, 1H) 7.70 (dd, J=7.80, 1.36 Hz, 1H) 8.61 (d, J=1.70 Hz, 1 H); MS (ESI) m/z 416 (M+H)$^+$, 414 (M−H)$^-$.

Example 21 methyl 1-[2-({[(2Z)-3-butyl-5-tert-butyl-1,3,4-thiadiazol-2(3H)-ylidene]amino}carbonyl)-4-(trifluoromethyl)benzyl]azetidine-3-carboxylate Example 21A (Z)-1-(2-(5-tert-butyl-3-butyl-1,3,4-thiadiazol-2(3H)-ylidenecarbamoyl)-4-(trifluoromethyl)benzyl)azetidine-3-carboxylic acid The title compound was prepared and isolated as described in Example 9I, substituting Example 16E for Example 9H, and substituting methyl azetidine-3-carboxylate hydrochloride for azetidin-3-ol hydrochloride in 46% yield. $^1$H NMR (300 MHz, CDCl$_3$) δ ppm 1.00 (t, 3H) 1.35-1.42 (m, 2H) 1.44 (s, 9H) 1.86-1.98 (m, 2H) 3.28-3.40 (m, 1H) 4.03 (t, J=9.52 Hz, 2H) 4.34 (dd, J=9.72, 4.56 Hz, 2H) 4.43 (t, J=7.14 Hz, 2H) 4.82 (s, 2H) 7.75 (dd, J=8.13, 1.78 Hz, 1H) 7.97 (d, J=8.33 Hz, 1H) 8.59 (d, J=1.59 Hz, 1H); (ESI) m/z 499 (M+H)$^+$, 497 (M−H)$^-$.

Example 21B methyl 1-[2-({[(2Z)-3-butyl-5-tert-butyl-1,3,4-thiadiazol-2(3H)-ylidene]amino}carbonyl)-4-(trifluoromethyl)benzyl]azetidine-3-carboxylate To a solution of Example 21A (200 mg, 0.401 mmol) in MeOH was added (diazomethyl)trimethylsilane (1 mL, 2M in ether). The reaction was concentrated to obtain the title compound (170 mg, 0.332 mmol, 83% yield). $^1$H NMR (300 MHz, CDCl$_3$) δ ppm 0.96-1.04 (m, 3H) 1.35-1.47 (m, 2H) 1.43 (s, 9H) 1.85-1.96 (m, 2H) 3.29-3.50 (m, 3H) 3.54-3.67 (m, 2H) 3.71 (s, 3H) 4.26 (s, 2H) 4.41 (t, J=7.12 Hz, 2H) 7.64-7.79 (m, 2H) 8.48 (s, 1H); (ESI) m/z 513 (M+H)$^-$, 511 (M−H)$^-$.

Example 22

N-[(2Z)-3-butyl-5-tert-butyl-1,3,4-thiadiazol-2(3H)-ylidene]-2-{[3-(1-hydroxy-1-methylethyl)azetidin-1-yl]methyl}-5-(trifluoromethyl)benzamide To a solution of Example 21B (140 mg, 0.273 mmol) in THF (4 ml) was added methylmagnesium bromide (130 mg, 1.092 mmol) at 0° C. (1 mL, 1.4M solution in toluene/THF 75:25), monitored by LC/MS until starting material was consumed. The reaction was quenched with NH$_4$Cl, and extracted with dichloromethane. The organic layers were washed with brine, concentrated and purified by chromatography using an Analogix® Intelliflash280™ (SiO$_2$, 0-30% solvent A in EtOAc, solvent A=9:1 MeOH:NEt$_3$) to give title compound (20 mg, 0.039 mmol, 14.28% yield). $^1$H NMR (500 MHz, CDCl$_3$) δ ppm 1.00 (t, J=7.32 Hz, 3H) 1.14 (s, 6H) 1.39-1.43 (m, 2H) 1.44 (s, 9H) 1.84-1.97 (m, 2H) 2.60-2.74 (m, 1H) 3.80 (t, J=9.00 Hz, 2H) 3.85-3.96 (m, 2H) 4.43 (t, J=7.32 Hz, 2H) 4.63 (s, 2H) 5.27-5.41 (m, J=11.60 Hz, 1H) 7.64-7.86 (m, 2H) 8.53 (s, 1H); (ESI) m/z 513 (M+H)$^+$, 511 (M−H)$^-$.

Example 23 tert-butyl[2-({[(3E)-2-butyl-5-tert-butyl-1-methyl-1,2-dihydro-3H-pyrazol-3-ylidene]amino}carbonyl)-4-(trifluoromethyl)phenyl]acetate Example 23A (E)-2-bromo-N-(5-tert-butyl-2-butyl-1-methyl-1H-pyrazol-3(2H)-ylidene)-5-(trifluoromethyl)benzamide The title compound was prepared and isolated as described in Example 3F, substituting Example 1D for Example 3E in 43% yield. $^1$H NMR (300 MHz, DMSO-d$_6$) δ ppm 0.89 (t, J=7.29 Hz, 3H) 1.29 (dq, J=14.71, 7.30 Hz, 2H) 1.39 (s, 9H) 1.56-1.68 (m, 2H) 3.88 (s, 3H) 4.27 (t, J=7.29 Hz, 2H) 6.81 (s, 1H) 7.55 (dd, J=8.31, 1.86 Hz, 1H) 7.80 (d, J=8.48 Hz, 1H) 7.87 (d, J=2.03 Hz, 1H); MS (DCI/NH$_3$) m/z 360 (M+H)$^+$.

Example 23B tert-butyl[2-({[(3E)-2-butyl-5-tert-butyl-1-methyl-1,2-dihydro-3H-pyrazol-3-ylidene]amino}carbonyl)-4-(trifluoromethyl)phenyl]acetate A solution of (2-tert-butoxy-2-oxoethyl)zinc(II) bromide (5.21 ml, 2.61 mmol) in ether (3 mL) was added to Example 23A (0.6 g, 1.303 mmol). Palladium acetate (0.029 g, 0.130 mmol), and dicyclohexyl(2',6'-dimethoxybiphenyl-2-yl)phosphine (0.082 g, 0.2 mmol) were added and the mixture was heated at 70° C. for 72 hours. The reaction was quenched with saturated aqueous NH$_4$Cl and extracted by EtOAc (3×10 mL). The organic layers were combined, washed with water, dried, concentrated and the residue was purified by column chromatography using an Analogix® Intelliflash280™ (15-100% solvent B in hexane, solvent B: 5% NEt$_3$ and 10% MeOH in EtOAc) to afford the title compound (150 mg, 23%). $^1$H NMR (300 MHz, CDCl$_3$) δ ppm 0.97 (t, J=7.29 Hz, 3H) 1.40-1.42 (m, 20H) 1.61-1.75 (m, 2H) 3.74 (s, 3H) 4.20 (s, 2H) 4.24-4.32 (m, 2H) 7.01 (s, 1H) 7.30 (d, J=8.14 Hz, 1H) 7.51 (dd, J=7.97, 1.53 Hz, 1H) 8.41 (d, J=1.70 Hz, 1H); MS (DCI/NH$_3$) m/z 496 (M+H)$^+$.

Example 24

N-[(3E)-2-butyl-5-tert-butyl-1-methyl-1,2-dihydro-3H-pyrazol-3-ylidene]-2-[(3-hydroxyazetidin-1-yl)methyl]-5-(trifluoromethyl)benzamide The title compound was prepared and isolated as described in Example 9I, substituting Example 12A for Example 9H in 12% yield. $^1$H NMR (500 MHz, CD$_3$OD) δ ppm 0.98 (t, J=7.48 Hz, 3H) 1.35-1.44 (m, 2H) 1.48 (s, 9H) 1.68-1.80 (m, 2H) 3.56-3.65 (m, 2H) 3.99 (s, 3H) 4.04-4.14 (m, 2H) 4.36-4.45 (m, 4H) 4.51-4.62 (m, 1H) 4.87 (s, 1H) 6.89 (s, 1H) 7.61-7.81 (m, 2H) 8.32 (s, 1H); (ESI) m/z 467 (M+H)$^+$, 465 (M−H)$^-$.

Example 25

N-[(3E)-2-butyl-5-tert-butyl-1-methyl-1,2-dihydro-3H-pyrazol-3-ylidene]-2-[(2-hydroxy-2-methylpropoxy)methyl]-5-(trifluoromethyl)benzamide

Example 25A 1-bromo-2-(bromomethyl)-4-(trifluoromethyl)benzene

To a solution of (2-bromo-5-(trifluoromethyl)phenyl)methanol (1.6 g, 6.27 mmol) in dichloromethane (10 mL) at 0° C. was added tribromophosphine (1.698 g, 6.27 mmol) over 2 hours. To the reaction mixture was added saturated NaHCO$_3$ and the organic layers was separated, dried with NaSO$_4$, filtered, and concentrated. The residue was purified by column chromatography using an Analogix® Intelliflash280™ (SiO$_2$, 0-100% EtOAc in hexane) to afford the title compound (1.2 g, 3.77 mmol, 60.2% yield). $^1$H NMR (300 MHz, CDCl$_3$) δ ppm 4.60 (s, 2H) 7.53-7.61 (m, 2H) 7.84 (s, 1H).

Example 25B 2-methylpropane-1,2-diol

To a solution of methyl 2-hydroxy-2-methylpropanoate (9.68 mL, 85 mmol) in THF (100 mL) at 0° C. was added lithium aluminum hydride (9.64 g, 254 mmol) portion wise over 20 min. This mixture was stirred at room temperature for 12 hours. The reaction was carefully quenched with H$_2$O (2 mL), 10% NaOH (2 mL) and H$_2$O (6 ml). The solid was filtered and washed with THF (20 mL). The filtrate was dried, concentrated, and used without purification. $^1$H NMR (400 MHz, DMSO-d$_6$) δ ppm 1.03 (s, 6H) 3.13 (d, J=5.83 Hz, 2H) 4.04 (s, 1H) 4.45 (t, J=5.83 Hz, 1H).

Example 25C 1-(2-bromo-5-(trifluoromethyl)benzyloxy)-2-methylpropan-2-ol

To a suspension of sodium hydride (0.138 g, 5.77 mmol) in THF (10 ml) at 0° C. was added Example 25B (0.208 g, 2.307 mmol). After stirring for 1 hour, Example 25A (0.88 g, 2.77 mmol) was added to the reaction and the mixture was stirred for 16 hours. The mixture was quenched with saturated NH$_4$Cl (30 mL), and the solvent was removed in vacuo. The residue was partitioned between water and ether, and the ether layer was separated, dried (MgSO$_4$), filtered, and concentrated. The crude product was purified by column chromatography using an Analogix® Intelliflash280™ (SiO$_2$, 0-100% EtOAc in hexane) to afford the title compound (0.468 g, 62%). $^1$H NMR (300 MHz, CDCl$_3$) δ ppm 1.27 (s, 6H) 3.43 (s, 2H) 4.66 (s, 2H) 7.57-7.65 (m, 2H) 7.81 (s, 1H).

Example 25D methyl 2-((2-hydroxy-2-methylpropoxy)methyl)-4-(trifluoromethyl)benzoate To a solution of Example 25C (20 mg, 0.061 mmol) in MeOH (10 mL) was added to Pd-dppf (Heraeus) (0.895 mg, 1.223 μmol) and NEt$_3$ (0.017 ml, 0.122 mmol) in a 50 ml pressure bottle. The mixture was pressurized with Hydrogen/Carbon Monoxide (60 psi), and stirred at 60° C. for 4 hours, at 80° C. for 4 hours, and at 100° C. for 16 hours. The reaction mixture was concentrated, taken up in EtOAc and filtered. The filtrate was concentrated and the residue was purified by column chromatography using an Analogix® Intelliflash280™ (SiO$_2$, 0-100% EtOAc in hexane) to afford the title compound. $^1$H NMR (300 MHz, CDCl$_3$) δ ppm 1.27 (s, 6H) 3.43 (s, 2H) 3.93 (s, 3H) 5.00 (s, 2H) 7.76-7.85 (m, 2H) 8.21 (s, 1H); MS (DCI/NH$_3$) m/z 324 (M+NH$_4$)$^+$.

Example 25E 2-((2-hydroxy-2-methylpropoxy)methyl)-4-(trifluoromethyl)benzoic acid To a solution of Example 25D (456 mg, 1.489 mmol) in MeOH (3 mL) was added sodium hydroxide (179 mg, 4.47 mmol) in H$_2$O (0.7 mL) and stirred for 12 hours. To the reaction mixture was added HCl (2N, 5 mL) and the mixture was extracted with EtOAc (2×10 mL). The organic layers were combined, dried with NaSO$_4$, filtered, concentrated and used without further purification. $^1$H NMR (300 MHz, CDCl$_3$) δ ppm 1.29 (s, 6H) 3.47 (s, 2H) 5.01 (s, 2H) 7.80-7.83 (m, 2H) 8.31 (s, 1H); MS (DCI/NH$_3$) m/z 310 (M+NH$_4$).

Example 25F

N-[(3E)-2-butyl-5-tert-butyl-1-methyl-1,2-dihydro-3H-pyrazol-3-ylidene]-2-[(2-hydroxy-2-methylpropoxy)methyl]-5-(trifluoromethyl)benzamide To a solution of Example 1D (0.112 g, 0.534 mmol) in THF (2 ml) was added Example 25E (0.130 g, 0.445 mmol), triethylamine (0.310 ml, 2.224 mmol) followed by addition of 1-propanephosphonic acid cyclic anhydride 50% solution in ethyl acetate (Aldrich) (0.847 ml, 1.423 mmol) and stirred overnight. The reaction was washed with saturated NaHCO$_3$, dried, filtered, concentrated and the residue purified by column chromatography using an Analogix® Intelliflash280™ (SiO$_2$, 15-100% solvent B in hexane, solvent B: 5% NEt$_3$ and 10% MeOH in EtOAc) to afford the title compound (32 mg, 0.066 mmol, 14.88% yield). $^1$H NMR (300 MHz, CDCl$_3$) δ ppm 0.99 (t, J=7.34 Hz, 3H) 1.23 (s, 6H) 1.38-1.46 (m, 11H) 1.71 (qd, J=7.60, 7.34 Hz, 2H) 3.40 (s, 2H) 3.77 (s, 3H) 4.23-4.34 (m, 2H) 5.18 (s, 2H) 7.01 (s, 1H) 7.58 (dd, J=7.93, 1.59 Hz, 1H) 7.65-7.75 (m, 1H) 8.34-8.36 (m, 1H); MS (DCI/NH$_3$) m/z 484 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound according to formula (I-i), or a pharmaceutically acceptable salt, solvate, salt of a solvate, prodrug, salt of a prodrug, or a combination thereof

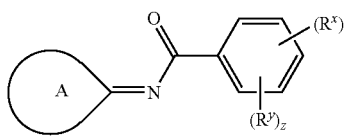

(I-i)

wherein

R$^x$ is —C(=NOR$^f$)R$^a$, —(CR$^{1a}$R$^{1b}$)$_{q1}$-A$^1$, alkenyl, or alkynyl; wherein the alkenyl and the alkynyl are substituted with one or two A$^2$ groups;

each R$^y$ is independently G$^{1d}$, alkyl, alkenyl, alkynyl, halogen, haloalkyl, =N—CN, =N—OR$^f$, NO$_2$, —CN, oxo, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N (R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(R$^f$)$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O) R$^f$, —(CR$^{1c}$R$^{1d}$)$_{q3}$—N(R$^2$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, or —(CR$^{1c}$R$^{1d}$)$_{q3}$—CN;

A$^1$ is —OR$^a$, —OC(O)R$^a$, —OC(O)N(R$^b$)(R$^c$), —N(R$^b$)(R$^k$), —C(O)O(R$^a$), —C(O)R$^a$, —S(O)$_2$R$^d$, —S(O)R$^d$, —SR$^d$, —C(O)N(R$^b$)(R$^c$), —C(S)N(R$^b$)(R$^c$), —S(O)$_2$N(R$^b$)(R$^c$), —C(=NOR$^f$)R$^a$, —CN, —N(R$^c$)C(O)R$^a$, —N(R$^c$)C(O)OR$^d$, —N(R$^c$)S(O)$_2$R$^d$, —N(R$^c$)C(O)N(R$^b$)(R$^c$), —N(R$^c$)S(O)$_2$N(R$^b$)(R$^c$), G$^{1a}$ or G$^{1b}$;

each occurrence of A$^2$ is independently —OR$^a$, —OC(O)R$^a$, —OC(O)N(R$^b$)(R$^c$), —N(R$^b$)(R$^k$), —C(O)O(R$^a$), —C(O)R$^a$, —S(O)$_2$R$^d$, —S(O)R$^d$, —SR$^d$, —C(O)N(R$^b$)(R$^c$), —C(S)N(R$^b$)(R$^c$), —S(O)$_2$N(R$^b$)(R$^c$), —C(=NOR$^f$)R$^a$, —CN, —N(R$^c$)C(O)R$^a$, —N(R$^c$)C(O)OR$^d$, —N(R$^c$)S(O)$_2$R$^d$, —N(R$^c$)C(O)N(R$^b$)(R$^c$), —N(R$^c$)S(O)$_2$N(R$^b$)(R$^c$), or G$^{1c}$;

G$^{1a}$ is a 4-, 5-, 6-, or 7-membered monocyclic heterocycle having zero double bond and one or two heteroatoms in the ring, wherein each ring is substituted with 1, 2, or 3 substituents independently selected from the group consisting of oxo, alkyl, alkenyl, alkynyl, haloalkyl, —OH, alkoxy, —C(O)O(alkyl), and hydroxyalkyl;

G$^{1b}$ is optionally substituted cycloalkyl or optionally substituted cycloalkenyl;

G$^{1c}$ is cycloalkyl, cycloalkenyl, aryl, heterocycle, or heteroaryl;

each ring as represented by G$^{1b}$ and G$^{1c}$ is optionally substituted with 1, 2, 3, 4, 5, or 6 substituents independently selected from the group consisting of oxo, alkyl, alkenyl, alkynyl, halogen, haloalkyl, =N—CN, —C(=NOR$^f$)R$^a$, =N—OR$^f$, —CN, NO$_2$, oxo, —OR$^a$, —OC(O)R$^a$, —OC(O)N(R$^b$)(R$^c$), —S(O)R$^d$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R)C(O)R$^a$, —N(R$^c$)S(O)$_2$R$^d$, —N(R$^c$)C(O)OR$^a$, —N(R)S(O)$_2$N(R$^b$)(R$^c$), —N(R$^c$)C(O)N(R$^b$)(R$^c$), —(CR$^{1c}$R$^{1d}$)$_{q3}$—OR$^a$, —(CR$^{1c}$R$^{1d}$)$_{q3}$—OC(O)R$^a$, —(CR$^{1c}$R$^{1d}$)$_{q3}$—OC(O)N(R$^b$)(R$^c$), —(CR$^{1c}$R$^{1d}$)$_{q3}$—S(O)R$^d$, —(CR$^{1c}$R$^{1d}$)$_{q3}$—S(O)$_2$R$^d$, —(CR$^{1c}$R$^{1d}$)$_{q3}$—S(O)$_2$N(R$^b$)(R$^c$), —(CR$^{1c}$R$^{1d}$)$_{q3}$—C(O)R$^a$, —(CR$^{1c}$R$^{1d}$)$_{q3}$—C(O)OR$^a$, —(CR$^{1c}$R$^{1d}$)$_{q3}$—C(O)N(R$^b$)(R$^c$), —(CR$^{1c}$R$^{1d}$)$_{q3}$—N(R$^b$)(R$^c$), —(CR$^{1c}$R$^{1d}$)$_{q3}$—N(R$^c$)C(O)R$^a$, —(CR$^{1c}$R$^{1d}$)$^{q3}$—N(R$^c$)S(O)$_2$R$^d$, —(CR$^{1c}$R$^{1d}$)$_{q3}$—N(R$^c$)C(O)O(R$^a$), —(CR$^{1c}$R$^{1d}$)$_{q3}$—N(R$^c$)S(O)$_2$N(R$^b$)(R$^c$), —(CR$^{1c}$R$^{1d}$)$_{q3}$—N(R$^c$)C(O)N(R$^b$)(R$^c$), and —(CR$^{1c}$R$^{1d}$)$_{q3}$—CN;

R$^a$ and R$^c$, at each occurrence, are each independently hydrogen, alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^b$, at each occurrence, is independently hydrogen, alkyl, haloalkyl, alkoxyalkyl, monocyclic cycloalkyl, —(CR$^{1a}$R$^{1b}$)$_{q3}$-(monocyclic cycloalkyl), or haloalkoxyalkyl;

R$^d$, at each occurrence, is independently alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

G$^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —N(R$^h$)$_2$, —CN, oxo, alkyl, haloalkyl, alkoxy, haloalkoxy, halogen, and —OH;

each occurrence of A$^3$ is independently C(O)R$^h$, —S(O)$_2$R$^e$, —C(O)N(R$^h$)$_2$, —C(S)N(R$^h$)$_2$, —S(O)$_2$N(R$^h$)$_2$, —C(=NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N(R$^h$)$_2$, —CN, —OR$^h$, or —N(R$^h$)$_2$;

R$^e$, at each occurrence, is independently C$_1$-C$_4$ alkyl, C$_1$-C$_4$ haloalkyl, monocyclic cycloalkyl, monocyclic heterocycle, or —(CR$^{1c}$R$^{1d}$)$_{q3}$-(monocyclic cycloalkyl);

R$^f$, at each occurrence, is independently hydrogen, C$_1$-C$_4$ alkyl, C$_1$-C$_4$ haloalkyl, monocyclic heterocycle, monocyclic cycloalkyl, or —(CR$^{1c}$R$^{1d}$)$_{q3}$-(monocyclic cycloalkyl);

R$^k$ is haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^{k'}$ is hydrogen, alkyl, haloalkyl, —(CR$^{1a}$R$^{1b}$)$_{q3}$-A$^3$, G$^{1d}$, or —(CR$^{1a}$R$^{1b}$)$_{q3}$-G$^{1d}$;

R$^h$, at each occurrence, is independently hydrogen, C$_1$-C$_4$ alkyl, C$_1$-C$_4$ haloalkyl, monocyclic heterocycle, monocyclic cycloalkyl, or —(CR$^{1c}$R$_{1d}$)$_{q3}$-(monocyclic cycloalkyl);

Ring A represents formula

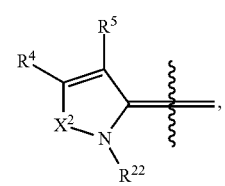

(b)

R$^{22}$ is alkyl, alkenyl, alkynyl, haloalkyl, —(CR$^{2a}$R$^{2b}$)$_{q4}$—OH, —(CR$^{2a}$R$^{2b}$)$_{q4}$—O-alkyl, —(CR$^{2a}$R$^{2b}$)$_{q4}$—O-haloalkyl, —(CR$^{2a}$R$^{2b}$)$_{q4}$—O-G$^{2a}$, —(CR$^{2a}$R$^{2b}$)$_{q4}$—O—(CR$^{2c}$R$^{2d}$)$_{q3}$-G$^{2a}$, —(CR$^{2a}$R$^{2b}$)$_{q5}$—C(O)—R$^a$, —(CR$^{2a}$R$^{2b}$)$_{q5}$—C(O)O(R$^a$), —(CR$^{2a}$R$^{2b}$)$_{q5}$—C(=N—OR$^f$)R$^a$, —(CR$^{2a}$R$^{2b}$)$_{q5}$—SO$_2$—R$^d$, —(CR$^{2a}$R$^{2b}$)$_{q5}$-G$^{2b}$, —(CR$^{2a}$R$^{2b}$)$_{q5}$—C(O)N(R$^b$)(R$^c$), or —(CR$^{2a}$R$^{2b}$)$_{q5}$—CN;

each occurrence of G$^{2a}$ is independently cycloalkyl, heterocycle, aryl, or heteroaryl;

G$^{2b}$ is a monocyclic cycloalkyl, monocyclic cycloalkenyl, thienyl, or phenyl; each of which is optionally fused with a benzo, a monocyclic cycloalkyl, a monocyclic cycloalkenyl, a monocyclic heterocycle, or a monocyclic heteroaryl;

$G^{2a}$ and $G^{2b}$, at each occurrence, are each independently unsubstituted or substituted with 1, 2, 3, 4, 5, or 6 substituents independently selected from the group consisting of oxo, alkyl, halogen, —OH, alkoxy, haloalkoxy, and haloalkyl;

$R^4$, and $R^5$ are each independently $G^3$, hydrogen, alkyl, alkenyl, alkynyl, —NO$_2$, —CN, halogen, —OR$^h$, —N(R$^h$)$_2$, —C(O)R$^h$, —C(O)O(R$^h$), haloalkyl, —(CR$^{3a}$R$^{3b}$)$_{q6}$—OR$^h$, —(CR$^{3a}$R$^{3b}$)$_{q6}$—N(R$^b$)$_2$, —(CR$^{3a}$R$^{3b}$)$_{q6}$—C(O)R$^h$, or —(CR$^{3a}$R$^{3b}$)$_{q6}$—C(O)O(R$^h$);

$G^3$, at each occurrence, is independently cycloalkyl, cycloalkenyl, aryl, heterocycle or heteroaryl, wherein each $G^3$ is independently unsubstituted or substituted with 1, 2, 3 or 4 substituents selected from the group consisting of $C_1$-$C_4$ alkyl, $C_2$-$C_4$ alkenyl, $C_1$-$C_4$ alkynyl, halogen, $C_1$-$C_4$ haloalkyl, =N—CN, =N—OR$^h$, —CN, oxo, —OR$^h$, —OC(O)R$^h$, —OC(O)N(R$^h$)$_2$, —S(O)$_2$R$^e$, —S(O)$_2$N(R$^h$)$_2$, —C(O)R$^h$, —C(O)OR$^h$, —C(O)N(R$^h$)$_2$, —N(R$^h$)$_2$, —N(R$^h$)C(O)R$^h$, —N(R$^h$)S(O)$_2$R$^c$, —N(R$^h$)C(O)O(R$^e$), and —N(R$^h$)C(O)N(R$^h$)$_2$;

$R^{1a}$, at each occurrence, is independently hydrogen, halogen, $C_1$-$C_4$ alkyl, or $C_1$-$C_4$ haloalkyl;

$R^{1b}$, at each occurrence, is independently hydrogen, halogen, $C_1$-$C_4$ alkyl, $C_1$-$C_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

$R^{1c}$, $R^{1d}$, $R^{2a}$, $R^{2b}$, $R^{2c}$, $R^{2d}$, $R^{3a}$ and $R^{3b}$, at each occurrence, are each independently hydrogen, halogen, $C_1$-$C_4$ alkyl, or $C_1$-$C_4$ haloalkyl;

$X^2$ is N(R$^{10}$) wherein R$^{10}$ is alkyl, alkoxyalkyl, haloalkoxyalkyl, or haloalkyl;

q1 and q3, at each occurrence, are each independently 1, 2, 3, or 4;

q4, at each occurrence, is independently 2, 3, 4, or 5;

q5 and q6, at each occurrence, are each independently 1, 2, 3, 4, 5, or 6;

z is 0, 1, 2, 3, or 4; and the monocyclic cycloalkyl and the monocyclic heterocycle, as a substituent or as part of a substituent, of R$^b$, R$^e$, R$^f$, and R$^h$, are each independently unsubstituted or substituted with 1, 2, 3, or 4 substituents independently selected from the group consisting of oxo, $C_1$-$C_4$ alkyl, halogen, —OH, $C_1$-$C_4$ alkoxy, $C_1$-$C_4$ haloalkoxy, and $C_1$-$C_4$ haloalkyl;

with the proviso that when R$^x$ is —(CR$^{1a}$R$^{1b}$)$_{q1}$-A$^1$, R$^{1a}$ and R$^{1b}$ are each independently hydrogen or alkyl, and A$^1$ is OR$^a$ wherein R$^a$ is G$^{1d}$, then G$^{1d}$ is other than phenyl; and with the further proviso that when R$^x$ is —(CR$^{1a}$R$^{1b}$)$_{q1}$-A$^1$, R$^{1a}$ and R$^{1b}$ are each independently hydrogen or alkyl, and A$^1$ is OC(O)R$^a$, then R$^a$ is other than alkyl.

2. The compound according to claim 1 having formula (I-i) or a pharmaceutically acceptable salt, solvate, salt of a solvate, prodrug, salt of a prodrug, or a combination thereof, wherein R$^x$ is —(CR$^{1a}$R$^{1b}$)$_{q1}$-A$^1$ or alkenyl substituted with one A$^2$ group; and each R$^y$, if present, is independently alkyl, —CN, haloalkyl, —OH, —O($C_1$-$C_4$ alkyl), or halogen.

3. The compound according to claim 1 or a pharmaceutically acceptable salt, solvate, salt of a solvate, prodrug, salt of a prodrug, or a combination thereof, wherein R$^4$ is alkyl or optionally substituted $C_3$-$C_6$ cycloalkyl;
R$^5$ is hydrogen or halogen; and
R$^{10}$ is $C_1$-$C_4$ alkyl.

4. The compound according to claim 3 or a pharmaceutically acceptable salt, solvate, salt of a solvate, prodrug, salt of a prodrug, or a combination thereof, wherein R$^{22}$ is alkyl, —(CR$^{2a}$R$^{2b}$)$_{q4}$—OH, —(CR$^{2a}$R$^{2b}$)$_{q4}$—O-alkyl, —(CR$^{2a}$R$^{2b}$)$_{q4}$—O-haloalkyl, or —(CR$^{2a}$R$^{2b}$)$_{q5}$-G$^{2b}$.

5. The compound according to claim 4 or a pharmaceutically acceptable salt, solvate, salt of a solvate, prodrug, salt of a prodrug, or a combination thereof, wherein R$^x$ is —(CR$^{1a}$R$^{1b}$)$_{q1}$-A$^1$.

6. The compound according to claim 5 or a pharmaceutically acceptable salt, solvate, salt of a solvate, prodrug, salt of a prodrug, or a combination thereof, wherein A$^1$ is G$^{1a}$, and G$^{1a}$ is azetidinyl, pyrrolidinyl, piperidinyl, piperazinyl, tetrahydrofuranyl, tetrahydropyranyl, or morpholinyl, wherein each G$^{1a}$ is substituted with a group selected from —OH, hydroxyalkyl, or —C(O)O(alkyl), and each G$^{1a}$ is optionally further substituted with one or two substituents independently selected from the group consisting of alkyl and haloalkyl.

7. The compound according to claim 4 or a pharmaceutically acceptable salt, solvate, salt of a solvate, prodrug, salt of a prodrug, or a combination thereof, wherein R$^x$ is alkenyl substituted with one A$^2$ group.

8. The compound according to claim 5 or a pharmaceutically acceptable salt, solvate, salt of a solvate, prodrug, salt of a prodrug, or a combination thereof, wherein A$^1$ is —OR$^a$.

9. The compound according to claim 5 or a pharmaceutically acceptable salt, solvate, salt of a solvate, prodrug, salt of a prodrug, or a combination thereof, wherein A$^1$ is —C(O)O(R$^a$).

10. The compound according to claim 1 or a pharmaceutically acceptable salt, solvate, salt of a solvate, prodrug, salt of a prodrug, or a combination thereof, selected from the group consisting of N-[(3E)-2-butyl-5-tert-butyl-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-pentyl-1,2-dihydro-3H-pyrazol-3-ylidene]-2-(3-hydroxy-3-methylbutyl)-5-(trifluoromethyl)benzamide;

N-[(3E)-5-tert-butyl-2-(cyclopropylmethyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclopropylmethyl)-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-propyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclobutylmethyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(cyclobutylmethyl)-1-methyl-1,2-dihydro-3H-pyrazol-3-ylidene]-2-(3-hydroxy-3-methylbutyl)-5-(trifluoromethyl)benzamide;

N-[(3E)-5-tert-butyl-1-methyl-2-propyl-1,2-dihydro-3H-pyrazol-3-ylidene]-2-(3-hydroxy-3-methylbutyl)-5-(trifluoromethyl)benzamide;

N-[(3E)-5-tert-butyl-2-(cyclopropylmethyl)-1-methyl-1,2-dihydro-3H-pyrazol-3-ylidene]-2-[(3-hydroxyazetidin-1-yl)methyl]-5-(trifluoromethyl)benzamide;

N-[(3E)-5-tert-butyl-2-(cyclopropylmethyl)-1-methyl-1,2-dihydro-3H-pyrazol-3-ylidene]-2-[(3-hydroxy-3-methylazetidin-1-yl)methyl]-5-(trifluoromethyl)benzamide;

ethyl 3-[2-({[(3E)-2-butyl-5-tert-butyl-1-methyl-1,2-dihydro-3H-pyrazol-3-ylidene]amino}carbonyl)-4-(trifluoromethyl)phenyl]propanoate;

N-[(3E)-2-butyl-5-tert-butyl-1-methyl-1,2-dihydro-3H-pyrazol-3-ylidene]-2-[(3-hydroxy-3-methylazetidin-1-yl)methyl]-5-(trifluoromethyl)benzamide;

N-[(3E)-2-butyl-5-tert-butyl-1-methyl-1,2-dihydro-3H-pyrazol-3-ylidene]-2-{[(3R)-3-hydroxypyrrolidin-1-yl]methyl}-5-(trifluoromethyl)benzamide;

N-[(3E)-5-tert-butyl-2-(3-methoxypropyl)-1-methyl-1,2-dihydro-3H-pyrazol-3-ylidene]-2-[(1E)-3-hydroxy-3-methylbut-1-enyl]-5-(trifluoromethyl)benzamide;

N-[(3E)-5-tert-butyl-2-(3-methoxypropyl)-1-methyl-1,2-dihydro-3H-pyrazol-3-ylidene]-2-(3-hydroxy-3-methylbutyl)-5-(trifluoromethyl)benzamide; and tert-butyl[2-({[(3E)-2-butyl-5-tert-butyl-1-methyl-1,2-dihydro-3H-pyrazol-3-ylidene]amino}carbonyl)-4-(trifluoromethyl)phenyl]acetate;

N-[(3E)-2-butyl-5-tert-butyl-1-methyl-1,2-dihydro-3H-pyrazol-3-ylidene]-2-[(3-hydroxyazetidin-1-yl)methyl]-5-(trifluoromethyl)benzamide; and N-[(3E)-2-butyl-5-tert-butyl-1-methyl-1,2-dihydro-3H-pyrazol-3-ylidene]-2-[(2-hydroxy-2-methylpropoxy)methyl]-5-(trifluoromethyl)benzamide.

11. A pharmaceutical composition comprising a therapeutically effective amount of a compound of formula (I-i) according to claim 1 or a pharmaceutically acceptable salt, solvate, salt of a solvate, prodrug, salt of a prodrug, or a combination thereof, in combination with a pharmaceutically acceptable carrier.

12. A method for treating pain in a mammal in need of such treatment comprising administering to the mammal a therapeutically effective amount of a compound of formula (I-i) according to claim 1, or a pharmaceutically acceptable salt, solvate, salt of a solvate, prodrug, salt of a prodrug, or a combination thereof.

13. A method of treating neuropathic pain, nociceptive pain, inflammatory pain, cancer pain, or osteoarthritis pain in a mammal in need thereof, said method comprises administering to the mammal a therapeutically effective amount of a compound of formula (I-i) according to claim 1, or a pharmaceutically acceptable salt, solvate, salt of a solvate, prodrug, salt of a prodrug, or a combination thereof.

* * * * *